US010832035B2

United States Patent
Wang et al.

(10) Patent No.: US 10,832,035 B2
(45) Date of Patent: Nov. 10, 2020

(54) SUBJECT IDENTIFICATION SYSTEMS AND METHODS

(71) Applicant: KONINKLIJKE PHILIPS N.V., Eindhoven (NL)

(72) Inventors: Haibo Wang, Melrose, MA (US); Xiang Xiang, Eindhoven (NL); Kees van Zon, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 204 days.

(21) Appl. No.: 16/014,046

(22) Filed: Jun. 21, 2018

(65) Prior Publication Data
US 2018/0373925 A1 Dec. 27, 2018

Related U.S. Application Data

(60) Provisional application No. 62/523,434, filed on Jun. 22, 2017.

(51) Int. Cl.
*G06K 9/00* (2006.01)
*G06N 3/08* (2006.01)
(Continued)

(52) U.S. Cl.
CPC ..... *G06K 9/00288* (2013.01); *G06K 9/00268* (2013.01); *G06K 9/4628* (2013.01);
(Continued)

(58) Field of Classification Search
CPC ...... G06N 3/08; G06N 20/00; G06K 9/00288; G06K 9/00228; G06K 9/48; G06K 9/4628;
(Continued)

(56) References Cited

U.S. PATENT DOCUMENTS

| 8,165,282 B1 * | 4/2012 | Coughlan | H04M 3/523 379/265.11 |
| 2005/0147292 A1 * | 7/2005 | Huang | G06K 9/00228 382/159 |

(Continued)

FOREIGN PATENT DOCUMENTS

WO 2017011745 A1 1/2017

OTHER PUBLICATIONS

Parkhi, O. et al., "Deep Face Recognition", Visual Geometry Group, Department of Engineering Science, University of Oxford, 2015.
(Continued)

*Primary Examiner* — Jingge Wu

(57) ABSTRACT

Disclosed techniques relate to identifying subjects in digital images. In various embodiments, digital image(s) that depict a subject in an area may be acquired. Portion(s) of the digital image(s) that depict a face of the subject may be detected as detected face image(s). Features of each of the detected face image(s) may be compared with features of each of a set of subject reference templates associated with a given subject in a subject reference database. Based on the comparing, a subject reference template may be selected from the set of subject reference templates associated with the given subject. Similarity measure(s) may then be determined between a given detected face image of the detected face image(s) and the selected subject reference template. An identity of the subject may be determined based on the similarity measure(s).

20 Claims, 11 Drawing Sheets

(51) Int. Cl.
| | |
|---|---|
| *G06K 9/66* | (2006.01) |
| *G06K 9/62* | (2006.01) |
| *G16H 40/67* | (2018.01) |
| *G06K 9/46* | (2006.01) |
| *G08B 21/04* | (2006.01) |
| *G08B 5/36* | (2006.01) |
| *G16H 30/40* | (2018.01) |
| *G16H 40/20* | (2018.01) |
| *G16H 50/70* | (2018.01) |

(52) U.S. Cl.
CPC ......... *G06K 9/6215* (2013.01); *G06K 9/6276* (2013.01); *G06K 9/66* (2013.01); *G06N 3/08* (2013.01); *G08B 5/36* (2013.01); *G08B 21/043* (2013.01); *G16H 30/40* (2018.01); *G16H 40/20* (2018.01); *G16H 40/67* (2018.01); *G16H 50/70* (2018.01)

(58) Field of Classification Search
CPC .. G06K 9/6255; G06K 9/6267; G06K 9/6276; G06K 9/00268; G06K 9/66; G06K 9/00536; G06K 9/00087; G06K 9/00523; G16H 30/40; G16H 50/70; G16H 40/20; G16H 40/63; G16H 40/67; G08B 21/043; G08B 5/36
See application file for complete search history.

(56) References Cited

U.S. PATENT DOCUMENTS

| | | | | |
|---|---|---|---|---|
| 2005/0265581 | A1* | 12/2005 | Porter | G06K 9/00295 382/103 |
| 2006/0140455 | A1 | 6/2006 | Costache et al. | |
| 2006/0251339 | A1* | 11/2006 | Gokturk | G06K 9/00375 382/305 |
| 2008/0273766 | A1* | 11/2008 | Kim | G06K 9/00295 382/118 |
| 2008/0317294 | A1* | 12/2008 | Hashimoto | G07C 9/37 382/115 |
| 2010/0150408 | A1* | 6/2010 | Ishikawa | G06K 9/00288 382/118 |
| 2011/0081089 | A1* | 4/2011 | Mori | G06K 9/00281 382/218 |
| 2011/0091113 | A1* | 4/2011 | Ito | G06K 9/00248 382/197 |
| 2011/0135166 | A1* | 6/2011 | Wechsler | G06K 9/00288 382/118 |
| 2013/0259310 | A1* | 10/2013 | Tsukamoto | G06K 9/3241 382/103 |
| 2013/0266193 | A1* | 10/2013 | Tiwari | G06K 9/00771 382/115 |
| 2014/0253709 | A1* | 9/2014 | Bresch | A61B 5/0077 348/77 |
| 2015/0110349 | A1* | 4/2015 | Feng | G06K 9/00234 382/103 |
| 2015/0169938 | A1* | 6/2015 | Yao | G06K 9/6207 382/103 |
| 2015/0317511 | A1* | 11/2015 | Li | G06K 9/00288 382/118 |
| 2016/0086015 | A1* | 3/2016 | Irmatov | G06K 9/00281 382/103 |
| 2016/0140436 | A1 | 5/2016 | Yin et al. | |
| 2016/0292494 | A1* | 10/2016 | Ganong | G06K 9/00288 |
| 2017/0206403 | A1* | 7/2017 | Rambach | G06K 9/00288 |
| 2017/0262695 | A1* | 9/2017 | Ahmed | G06K 9/00288 |
| 2017/0308734 | A1* | 10/2017 | Chalom | G06T 3/40 |
| 2018/0068173 | A1* | 3/2018 | Kolleri | G01S 19/13 |
| 2018/0181834 | A1* | 6/2018 | Cui | G06Q 50/265 |
| 2018/0293429 | A1* | 10/2018 | Wechsler | G06K 9/00281 |

OTHER PUBLICATIONS

Wang, H. et al., "Monitoring Patients in the Wild", IEEE 12th International Conference on Automatic Face & Gesture Recognition, 2017.

* cited by examiner

SUBJECT IDENTIFICATION SYSTEMS AND METHODS

CROSS-REFERENCE TO RELATED APPLICATION

The present application claims the benefit of U.S. Provisional Application No. 62/523,434, filed Jun. 22, 2017. These applications are hereby incorporated by reference herein.

TECHNICAL FIELD

The present disclosure is directed generally, but not exclusively, to identifying people in digital images (including streams of digital images). More particularly, but not exclusively, various methods and apparatus disclosed herein relate to identifying people in digital images (or streams thereof) so that those people can be located in areas such as waiting rooms of a hospital.

BACKGROUND

There are a number of scenarios in which it may be desirable to automatically identify people (or "subjects") based on digital images that capture scenes containing people. For example, when patients visit a hospital, they typically are registered, triaged, and then sent to an area such as a waiting room to wait for hospital resources such as physicians to become available to examine and/or treat the patients. Being able to automatically identify individual patients may be helpful for continuing to monitor their conditions (e.g., for deterioration) while they wait for allocation of medical resources. It may also be helpful for determining if/when patients left without being seen (LWBS). Automatically identifying people based on digital images may also be useful in a variety of other contexts, such as airports, train stations, border crossings, gyms and fitness centers, various businesses, etc.

In some contexts, it may be desired to identify individual subjects in digital images that contain multiple subjects. For example, digital images captured by a camera in a waiting room are likely to depict, in addition to waiting patients, other people such as friends, relatives, etc. that might be waiting with the patients. Face detection techniques may detect all the faces in the digital images, but it may not be clear which faces belong to patients and which belong to others. Moreover, subjects in monitored areas such as waiting rooms are not likely going to be looking at the camera. Instead they may be looking at their phones, magazines, each other, etc. Thus, even when depicted faces are detected, the detected faces as depicted in their raw state may not be ideal for identifying subjects. In addition, the light conditions in the area may vary across time (e.g., daytime versus nighttime) and/or across the physical space.

SUMMARY

The present disclosure is directed to methods, systems, and apparatus for automatically identifying people depicted in acquired digital images. As one non-limiting example, a plurality of triaged patients may wait in a waiting room until they can be seen by an emergency medicine physician. The patients may be included in a patient monitoring queue (also referred to simply as a "patient queue") that is ordered or ranked, for instance, based on a measure of acuity associated with each patient (referred to herein as a "patient acuity measure") that is determined based on information obtained/acquired from the patient by a triage nurse, as well as other data points such as patient waiting time, patient presence, etc. One or more "vital sign acquisition cameras" mounted in the waiting room may be configured to periodically perform contactless and/or unobtrusive acquisition of one more updated vital signs and/or physiological parameters from each patient. These updated vital signs and/or physiological parameters may include but are not limited to temperature, pulse rate, oxygen saturation ("$SpO_2$"), respiration rate, posture, perspiration and so forth.

In order to identify a particular patient from which the vital sign acquisition camera(s) should acquire updated vital signs, techniques described herein may be employed to match so-called "subject reference templates"—e.g., digital images that depict a variety of different views of a subject's face—to a person contained in a scene captured in one or more digital images acquired by one or more vital sign acquisition cameras, e.g., from a relatively wide field of view ("FOV"). More generally, techniques described herein may be implemented in various contexts to identify subjects depicted in digital images (e.g., single images and/or streams of digital images, such as video feeds), e.g., by collecting subject reference templates associated with each subject to be monitored (which may be referred to herein as "registered subjects") and later using those subject reference templates to identify the subject in subsequently captured digital images.

Generally, in one aspect, a method may include: acquiring one or more digital images that depict a subject in an area; detecting, as one or more detected face images, one or more portions of the one or more digital images that depict a face of the subject; comparing features of each of the one or more detected face images with features of each of a set of subject reference templates associated with a given subject in a subject reference database, wherein the subject database stores subject reference templates related to a plurality of subjects; based on the comparing, selecting a subject reference template from the set of subject reference templates associated with the given subject; determining one or more similarity measures between a given detected face image of the one or more detected face images and the selected subject reference template; and determining an identity of the subject based on the one or more similarity measures.

In various embodiments, the comparing may include: applying the one or more detected face images as input across a neural network to generate one or more corresponding face feature vectors; and applying the set of subject reference templates associated with the given subject as input across the neural network to generate a plurality of corresponding template feature vectors. In various embodiments, the neural network comprises a convolutional neural network.

In various embodiments, the comparing may include calculating a plurality of distances between the one or more face feature vectors and the plurality of template feature vectors, wherein the calculating comprises calculating, for each template feature vector of the plurality of template feature vectors, a distance from each of the one or more face feature vectors. In various embodiments, the selecting may be based on a lowest distance of the plurality of distances. In various embodiments, the method may further include selecting the given detected face image from the one or more detected face images based on the lowest distance.

In various embodiments, the area may include a waiting room, and the one or more digital images that depict the waiting room may be acquired using a camera that is configured to capture the waiting room. In various embodiments, the comparing may include comparing features of each of the one or more detected face images with features of each of multiple sets of subject reference templates associated with the plurality of subjects. In various embodiments, the one or more similarity measures may include: a first similarity measure that is calculated based on a version of the given detected face image that is geometrically aligned with the selected subject reference template; and a second similarity measure that is calculated based directly on the given detected face image. In various embodiments, the identity of the subject may be determined based on the greater of the first and second similarity measures.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the disclosure.

DETAILED DESCRIPTION

Figure 1:
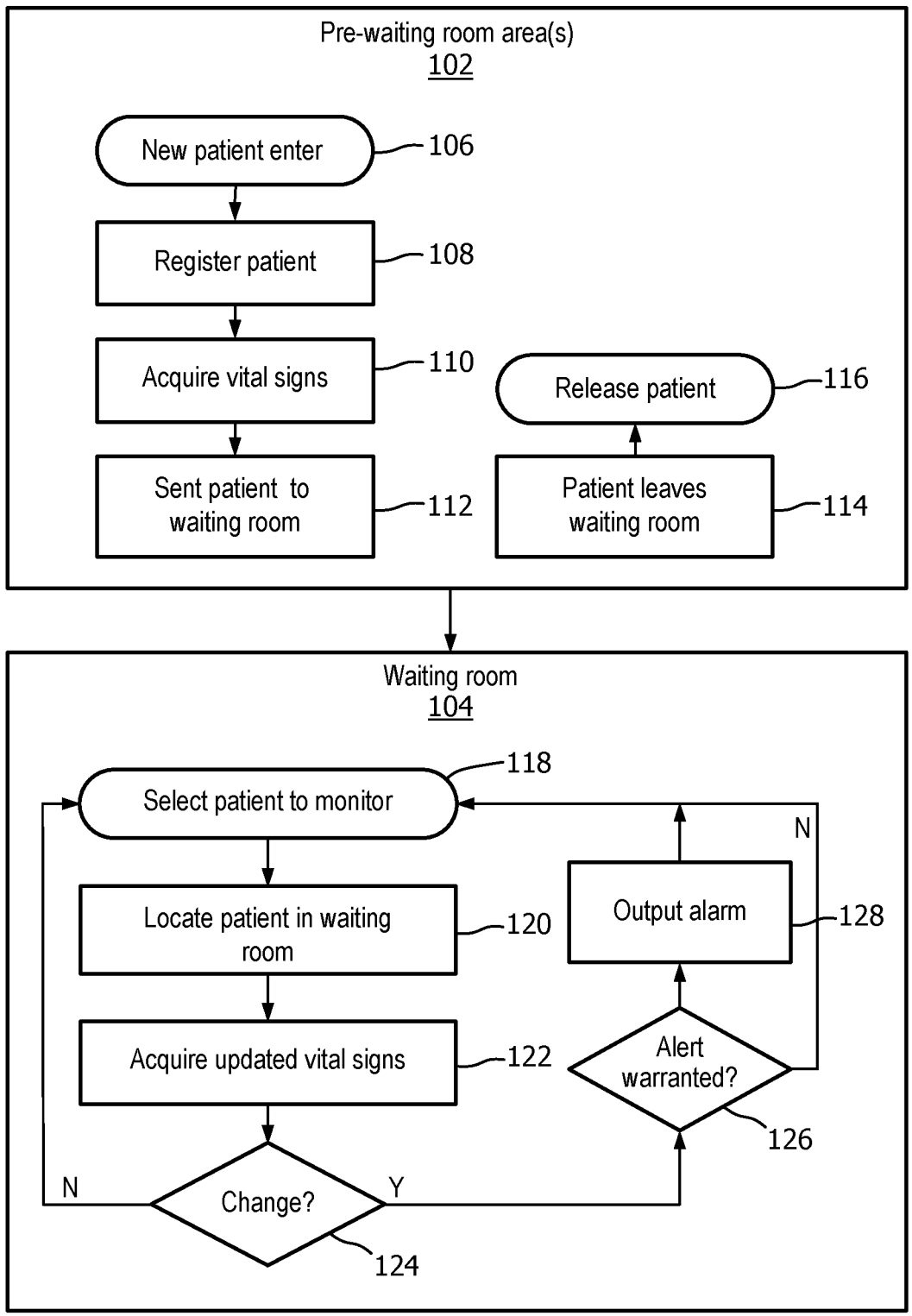
FIG. 1 schematically illustrates a general process flow for monitoring patients identified in digital images using disclosed techniques, in accordance with various embodiments.

FIG. 1 schematically illustrates generally how patients may be monitored using disclosed techniques. In particular, operations and actions are depicted that may occur in a pre-waiting room area, such as at a pre-waiting room area(s) 102, which may include reception and/or registration, and/or a triage station or booth. In addition, operations and actions are depicted that may occur in a waiting room 104. It should be understood that the sequence of FIG. 1 is not meant to be limiting, and other sequences are possible.

At block 106, a new patient may enter and/or approach pre-waiting room area(s) 102, e.g., after checking in at a reception desk (not depicted). At block 108, the new patient may be registered. Registration may include, for instance, collecting information about the patient such as the patient's name, age, gender, insurance information, and reason for visit. Typically, but not exclusively, this information may be manually input into a computer by medical personnel such as receptionist or registrar. In some embodiments, one or more reference digital images of the patient may be acquired, e.g., by a camera that is integral with a computing device operated by the triage nurse, by a standalone camera, and/or by a vital sign acquisition camera (in which case at least some vital signs may be optionally acquired at registration). As will be described in more detail below, in some embodiments, the digital images acquired by the camera during registration at block 108 may be referred to as "intake digital images." Subsets of these intake digital images—and in some cases, selected sub-portions of these images that depict, for instance, faces—may be selectively retained as "subject reference templates" that can be used later to identify patients (or more generally, "subjects") in areas such as waiting room 104.

In many instances, the triage nurse additionally may acquire various initial vital signs and/or physiological parameters at block 110 using various medical instruments. These initial vital signs and/or physiological parameters may include but are not limited to blood pressure, pulse, glucose level, $SpO_2$, photoplethysmogram ("PPG"), respiration rate (e.g., breathing rate), temperature, skin color, and so forth. While not depicted in FIG. 1, in some embodiments, other information may be gathered at triage as well, such as acquiring/updating a patient's medical history, determining patient allergies, determining patient's use of medications, and so forth. In some embodiments, the patient may be assigned a so-called "patient acuity measure," which may be a measure that is used to rank a severity of the patient's ailment, and in some instances may indicate an anticipated need for emergency room resources. Any number of commonly used indicators and/or clinician decision support ("CDS") algorithms may be used to determine and/or assign a patient acuity measure, including but not limited to the Emergency Severity Index ("ESI"), the Taiwan Triage System ("TTS"), the Canadian Triage and Acuity Scale ("CTAS"), and so forth. For example, in some embodiments, vital signs of the patient may be compared with predefined vital sign thresholds stored in a system database, or with published or known vital sign values typical for a given patient age, gender, weight, etc., to determine the patient's initial patient acuity measure and/or the patient's initial position in the patient queue. In some embodiments, various physiological and other information about the patient may be applied as input across a trained model (e.g., regression model, neural network, deep learning network, etc.), case-based reasoning algorithm, or other clinical reasoning algorithm to derive one or more acuity measures. In some embodiments, the information used for deriving the acuity measure may include or even be wholly limited to vitals or other information that may be captured by the vital sign acquisition camera. In some embodiments, the information used for deriving the acuity measure may alternatively or additionally include information such as information from a previous electronic medical record ("EMR") of the patient, information acquired from the patient at triage, information from wearable devices or other sensors carried by the patient, information about other patients or people in the waiting room (e.g., vitals of others in the room), information about family members or others associated with the patient (e.g., family member EMRs), etc.

Once the patient is registered and/or triaged, at block 112, the patient may be sent to waiting room 104. In many scenarios, the operations of FIG. 1 may occur in slightly different orders. For example, in some instances, a patient may first be registered, then go to a waiting room until they can be triaged, and then be sent to a doctor some time after triage (either immediately or after being sent back to the waiting room). In some situations, such as emergency situations (e.g., during disasters), patients may go straight to triage and then to a doctor, and may only be registered later when the patient has been stabilized.

At block 114, it may be determined, e.g., using one or more cameras, sensors, or input from medical personnel, that a patient has left the waiting room. Block 114 may include scanning each person currently within the waiting room (e.g., as part of a seeking function that attempts to locate the patient once the patient is at the top of a queue of patients for which vitals are to be captured, such as an execution of block 120 described below, or cycling through each person in the room to capture vitals, as multiple executions of the loop including blocks 118 and 120 described below) and determining that the patient was not located. In some embodiments, the system may wait until a predetermined number of instances of the patient missing is reached or a predetermined amount of time has passed during which the patient is missing before the patient is deemed to have left the waiting room to account for temporary absences (e.g., visiting the restroom or speaking with clinical staff). For example, the patient may have been taken into the ER proper because it is their turn to see a doctor. Or the patient's condition may have improved while they waited, causing them to leave the hospital. Or the patient may have become impatient and left to seek care elsewhere. Whatever the reason, once it is determined that the patient has left the waiting room for at least a threshold amount of time, at block 116, the patient may be deemed to have left without being seen and may be released from the system, e.g., by removing them from a queue in which registered patients are entered.

At block 118, one or more patients in waiting room 104 may be selected for monitoring. For example, in some embodiments, a database (e.g., subject reference database 412 in FIG. 4) storing registration information obtained at blocks 108-110 may be searched to select a patient having the highest patient acuity measure or a patient having the highest acuity measured that has not been monitored recently, as may be determined by a time threshold set for all patients or set (e.g., inversely correlated) based on the acuity measure. In other embodiments, registration information associated with a plurality of patients in the waiting room may be ranked in a patient monitoring queue, e.g., by their respective patient acuity measures, in addition to or instead of other measures such as waiting times, patient presence in the waiting room (e.g., missing patients may be selected for monitoring more frequently to determine whether they should be released if repeatedly absent), etc. In yet other embodiments, patient acuity measures may not be considered when ranking the patient monitoring queue, and instead only considerations of patient waiting times, patient presence, etc., may be considered. In still other embodiments, patients may simply be selected one-by-one, e.g., in a predetermined scanning order that is dictated, for instance, by a sequence of chairs or couches in waiting room 104.

However such a patient monitoring queue is ranked, in some embodiments, the first patient in the queue may be selected as the one to be monitored next. It is not required (though it is possible) that the patient monitoring queue be stored in sequence of physical memory locations ordered by patient acuity measures. Rather, in some embodiments, a ranked patient monitoring queue may merely include a rank or priority level value associated with each patient. In other words, a "patient monitoring queue" as described herein may refer to a "logical" queue that is logically ranked based on patient acuity measures, waiting time etc., not necessarily a contiguous sequence of memory locations. Patients may be selected for monitoring at block 118 in an order of their respective ranking in the patient monitoring queue.

At block 120, the patient selected at block 118 may be located in waiting room 104. In various embodiments, one or more cameras, such as one or more vital sign acquisition cameras (not depicted in FIG. 1, see FIGS. 2, and 3) or other more conventional cameras that are deployed in or near waiting room 104, may be operated (e.g., panned, tilted, zoomed, etc.) to acquire one or more digital images of patients in waiting room 104. As will be described in more detail below, those acquired digital images may be compared to one or more reference patient images (often referred to herein as "subject reference templates") captured during registration at block 108. In some embodiments, features of those acquired digital images that are extracted using a machine learning model, such as a trained convolutional neural network, may be compared to similarly-extracted features of subject reference templates associated with registered patients.

At block 122, one or more vital sign acquisition cameras mounted or otherwise deployed in or near waiting room 104 may be operated to perform unobtrusive (e.g., contactless) acquisition of one or more updated vital signs and/or physiological parameters from the patient selected at block 118 and located at block 120. These vital sign acquisition cameras may be configured to acquire (without physically contacting the patient) a variety of different vital signs and/or physiological parameters from the patient, including but not limited to blood pressure, pulse (or heart) rate, skin color, respiratory rate, $SpO_2$, temperature, posture, sweat levels, and so forth. In some embodiments, vital sign acquisition cameras may be equipped to perform so-called "contactless methods" to acquire vital signs and/or extract physiological information from a patient may be used as medical image devices. Non-limiting examples of such cameras are described in United States Patent Application Publication Nos. 20140192177A1, 20140139656A1, 20140148663A1, 20140253709A1, 20140235976A1, and U.S. Pat. No. 9,125, 606B2, which are incorporated herein by reference for all purposes.

At block 124, it may be determined, e.g., by one or more components depicted in FIG. 2 (described below), based on a comparison of the updated vital sign(s) and/or physiological parameters acquired at block 122 to previously-acquired vital signs and/or physiological parameters (e.g., the initial vital signs acquired at block 110 or a previous iteration of updated vital signs/physiological parameters acquired by the vital sign acquisition cameras), whether the patient's condition has changed. For example, it may be determined whether the patient's pulse rate, respiratory rate, blood pressure, $SpO_2$, PPG, temperature, etc. has increased or decreased while the patient has waited. If the answer is no, then control may proceed back to block 118, and a new patient (e.g., the patient with the next highest patient acuity measure) may be selected and control may proceed back to block 120. However, if the answer at block 124 is yes (i.e. the patient's condition has changed), then control may pass to block 126. In some embodiments, the patient's condition may be represented (at least partially) by the same acuity measure used for purposes of determining monitoring order.

At block 126, it may be determined (again, by one or more components of FIG. 2) whether a medical alert is warranted based on the change detected at block 124. For example, it may be determined whether a change in one or more vital signs or patient acuity measures satisfies one or more thresholds (e.g., has blood pressure increased above a level that is considered safe for this particular patient?). If the answer is yes, then control may pass to block 128. At block 128, an alarm may be output, e.g., to a duty nurse or other medical personnel, that the patient is deteriorating. The medical personnel may then check on the patient to determine if remedial action, such as immediately admitting to the ED to see a doctor, is warranted. In some embodiments, control may then pass back to block 118. However, if the answer at block 126 is no, then in some embodiments, control may pass back to block 118.

Figure 2:
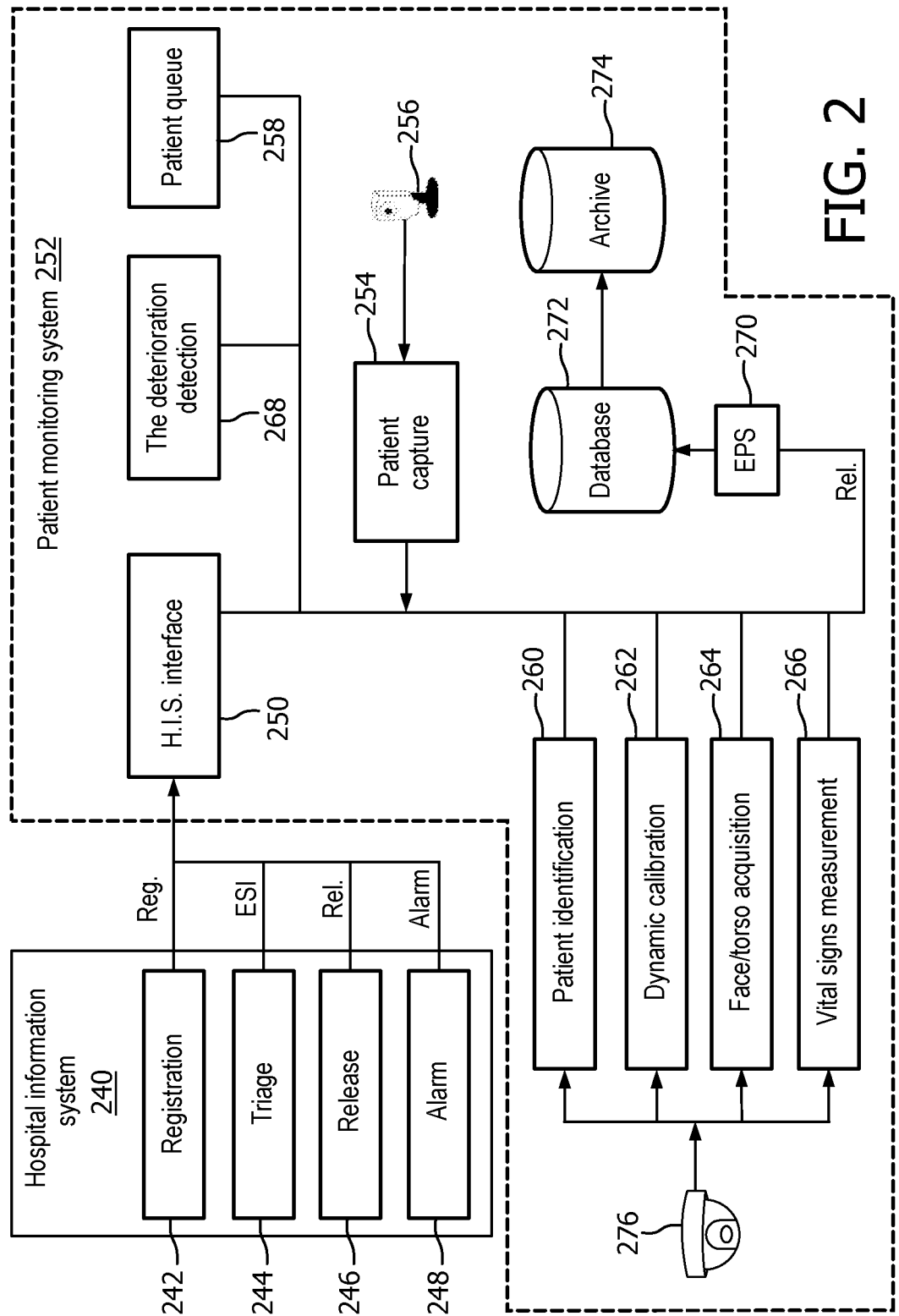
FIG. 2 illustrates an example environment in which various components of the present disclosure may implement selected aspects of the present disclosure, in accordance with various implementations.

FIG. 2 depicts example components that may be used to practice disclosed techniques, in accordance with various embodiments. A hospital information system 240 may be of the type that is commonly found in hospitals, doctor's offices, and so forth. Hospital information system 240 may be implemented using one or more computing systems that may or may not be connected via one or more computer networks (not depicted). Hospital information system 240 may include, among other things, a registration module 242, a triage module 244, a release module 246, and an alarm module 248. One or more of modules 242-248, or any other module or engine described herein, may be implemented using any combination of hardware and software, including one or more microprocessors executing instructions stored in memory. For example, the registration module 242 may include registration instructions implementing the functionality described herein in connection with registration executing on a processor while the triage module 244 may include triage instructions implementing the functionality described herein in connection with triage executing on the same processor. Similar underlying hardware and software may be used to implement other "modules" described herein.

Registration module 242 may be configured to receive, e.g., as manual input from a duty nurse, registration information of new patients. This may include, for instance, the patient's name, age, insurance information, and so forth. Triage module 244 may be configured to receive, e.g., as manual input from a duty nurse or directly from networked medical equipment, vital signs such as those described above and/or other physiological data, such as weight, height, the patient's reason for the visit, etc. In various embodiments, vital signs received by triage module 244 and/or a patient acuity measure (e.g., ESI in FIG. 2) may be associated with corresponding patient information received by registration module 242, e.g., in one or more databases (not depicted) associated with hospital information system 240.

Alarm module 248 may be configured to receive information indicative of various events, such as patient deterioration, and raise various alarms and/or alerts in response. These alarms and/or alerts may be output using a variety of modalities, including but not limited to visual output (e.g., on display screens visible to hospital personnel), intercom announcements, text messages, emails, audio alerts, haptic alerts, pages, pop-up windows, flashing lights, and so forth. Modules 242-248 of hospital information system 240 may be operably coupled, e.g., via one or computer networks (not depicted), to a hospital information system interface 250 ("H.I.S. Interface" in FIG. 2).

Hospital information system interface 250 may serve as an interface between the traditional hospital information system 240 and a patient monitoring system 252 configured with selected aspects of the present disclosure. In various embodiments, the hospital information system interface 250 may publish, e.g., to other modules of the patient monitoring system 252, various information about patients such as registration information, patient acuity measures (e.g., ESI), prescribed and/or administered medications, whether a patient has been released, various alarms/alerts, and so forth. As will be described below, in some embodiments, these publications may be provided to an event publish and subscribe ("EPS") module 270, which may then selectively store them in database 272 and/or selectively publish them to other modules of patient monitoring system 252. In some embodiments, hospital information system interface 250 may additionally or alternatively subscribe to one or more alerts or publications provided by other modules. For example, hospital information system interface 250 may subscribe to alerts from deterioration detection module 268, e.g., so that hospital information system interface 250 may notify appropriate components of hospital information system 240, such as alarm module 248, that a patient is deteriorating. EPS is just one of many possible protocols that could be used for communication among system components, and is not meant to be limiting.

Patient monitoring system 252 may include a variety of components that facilitate monitoring of patients in an area such as waiting room 104 to ensure that patients are served in a manner conducive with their actual medical condition. Patent monitoring system 252 may include, for instance, a patient capture module 254 that interfaces with one or more cameras 256, a patient queue module 258, a patient identification module 260, a dynamic calibration module 262, a face/torso acquisition module 264, a vital signs measurement module 266, a deterioration detection module 268, the aforementioned EPS module 270, and one or more databases 272, 274. As noted above, each of modules 250, 254, and 258-270 may be implemented using any combination of hardware and software. And while these modules are depicted separately, that is not meant to be limiting or to suggest each is implemented on a separate piece of hardware. For example, one or more modules may be combined and/or omitted, and one or more modules may be implemented on one or more computing systems operably connected via one or more computer networks (not depicted). The lines depicted connecting various components of FIG. 2 may represent communication channels accessible to these components. These communication channels may be implemented using any number of networking or other computer communication technologies, such as one or more buses, Ethernet, Wi-Fi, Bluetooth, Z-Wave, ZigBee, cellular communication, and so forth.

Patient monitoring system 252 may also include one or more vital sign acquisition cameras 276 that are configured to acquire, from some distance from a patient, one or more vital signs and/or physiological parameters of the patient. Examples of such vital sign acquisition cameras were described above. In various embodiments, a vital sign acquisition camera 276 may be a pan-tilt-zoom ("PTZ") camera that is operable to pan, tilt, and zoom so that different parts of an area such as waiting room 104 are contained within its FOV. In this manner, it is possible to scan the area being monitored to locate different patients, so that updated vital signs and/or physiological parameters may be acquired unobtrusively.

Patient capture module 254 may receive, from one or more cameras 256, one or more signals carrying captured image data of a patient. For example, in some embodiments, patient capture module 254 may receive a video stream from camera 256. Patient capture module 254 may perform image processing (e.g., face detection, segmentation, shape detection to detect human form, etc.) on the video stream to detect when a patient is present, and may capture one or more reference digital images of the patient (e.g., the intake digital images described below) in response to the detection. In some embodiments, the reference digital images may be captured at a higher resolution than individual frames of the video stream, although this is not required. In some embodiments, camera 256 may be a standalone camera, such as a webcam, a PTZ camera (e.g., 276), and so forth, that is deployed in or near pre-waiting room area(s) 102. Subsets of the intake digital images captured by camera 256 may be used to generate subject reference templates that are associated with registered patients (and more generally, "subjects") and used later to identify registered patients in the area being monitored.

Patient queue module 258 may be configured to establish and/or maintain a priority queue, e.g., in a database, of the order in which patients in the area should be monitored. In various embodiments, the queue may be ordered by various parameters. In some embodiments, patients in the queue may be ranked in order of patient acuity measures (i.e. by priority). For example, the most critical patients may be placed at the front of the queue more frequently than less critical patients. In some embodiments, updated vital signs may be acquired from patients waiting in the area being monitored, such as waiting room 104, in an order of the queue. In other embodiments, updated vital signs may be acquired from patients in a FIFO or round robin order. In other embodiments, updated vital signs may be acquired from patients in an order that corresponds to a predetermined scan trajectory programmed into vital sign acquisition camera 276 (e.g., scan each row of chairs in order).

Patient identification module 260 may be configured with selected aspects of the present disclosure to use one or more digital images captured by vital sign acquisition camera 276 (or another camera that is not configured to acquire vital signs unobtrusively), in conjunction with subject reference templates captured by patient capture module 254, to locate one or more patients in the area being monitored (e.g., waiting room 104). Patient identification module 260 may analyze acquired digital images using various techniques described below to identify and locate patients (subjects). FIGS. 4-10, described below, demonstrate various aspects of various techniques that may be employed as part of recognizing/identifying/locating patients, or more generally, subjects, in any context.

In some embodiments, patient identification module 260 may search an area being monitored for particular patients from which to obtain updated vital signs. For example, patient identification module 260 may search the area being monitored for a patient selected by patient queue module 258, which may be, for instance, the patient in the queue having the highest patient acuity measure. In some embodiments, patient identification module 260 may cause vital sign acquisition camera(s) 276 to scan the area being monitored (e.g., waiting room 104) until the selected patient is identified.

Dynamic calibration module 262 may be configured to track the use of vital sign acquisition camera(s) 276 and calibrate them as needed. For instance, dynamic calibration module 262 may ensure that whenever vital sign acquisition camera 276 is instructed to point to a particular PTZ location, it always points to the exact same place. PTZ cameras may be in constant or at least frequent motion. Accordingly, their mechanical components may be subject to wear and tear. Small mechanical errors/biases may accumulate and cause vital sign acquisition camera 276 to respond, over time, differently to a given PTZ command. Dynamic calibration module 262 may correct this, for instance, by occasionally running a calibration routine in which landmarks (e.g., indicia such as small stickers on the wall) may be used to train a correction mechanism that will make vital sign acquisition camera 276 respond appropriately Once a patient identified by patient queue module 258 is recognized/located by patient identification module 260, face/torso acquisition module 264 may be configured to pan, tilt, and/or zoom one or more vital sign acquisition cameras 276 so that their fields of view capture a desired portion of the patient. For example, in some embodiments, face/torso acquisition module 264 may pan, tilt, or zoom a vital sign acquisition camera 276 so that it is focused on a patient's face and/or upper torso. Additionally or alternatively, face/torso acquisition module 264 may pan, tilt, or zoom one vital sign acquisition camera 276 to capture predominantly the patient's face, and another to predominantly capture the patient's torso. Various vital signs and/or physiological parameters may then be acquired. For instance, vital signs such as the patient's pulse rate and $SpO_2$ may be obtained, e.g., by vital signs measurement module 266, by performing image processing on an video of the patient's face captured by vital sign acquisition camera(s) 276. Vital signs and/or physiological parameters such as the patient's respiratory rate, and so forth may be obtained, e.g., by vital signs measurement module 266, by performing image processing on an video of the patient's torso captured by vital sign acquisition camera(s) 276. Of course, the face and torso are just two examples of body portions that may be examined to obtain vital signs, and are not meant to be limiting.

Deterioration detection module 268 may be configured to analyze various signals and/or data to determine whether a condition of a registered patient (or even non-registered companions) is deteriorating, improving, and/or remaining stable. In some embodiments, the patient condition may be represented, at least in part, by the same patient acuity measures described above for determining order of patients for monitoring. As such, the deterioration detection module 268 may include one or more CDS, case-based reasoning, or other clinical reasoning algorithms as described herein or other clinical reasoning algorithms (e.g., trained logistic regression models or other machine learning models) for assessing patient condition measures other than acuity measures described herein. In some embodiments, the algorithms for assessing patient acuity or other measures of patient condition employed by the deterioration detection module 268 may be updated from time to time by, for example, writing new trained weights (e.g., theta values) for a selected machine learning model or providing new instructions for execution by a processor (e.g. in the form of a java archive, JAR, file or compiled library). These signals may include, for instance, a patient's initial vital signs and other physiological information (e.g., obtained at blocks 108-110 of FIG. 1), updated vital signs obtained by vital signs measurement module 266, a patients initial patient acuity measure (e.g., calculated during registration), and/or a patient's updated patient acuity measure (e.g., calculated based on updated vital signs and/or physiological parameters received from vital signs measurement module 266).

Based on determinations made using these data and/or signals, deterioration detection module 268 may send various alerts to various other modules to take various actions. For example, deterioration detection module 268 may publish an alert, e.g., by sending the alert to EPS module 270 so that EPS module can publish the alert to subscribed modules, such as alarm module 248 of hospital information system 240. In some embodiments, such an alert may include, for instance, a patient's name (or more generally, a patient identifier), a picture, live video stream, the patient's last detected location in the waiting room, baseline vital signs, one or more updated vital signs, and/or an indication of a patient acuity measure. On receipt of the alert, alarm module 248 may raise an alert or alarm to medical personnel of the patient's deterioration and, among other things, the patient's last detected location in the waiting room.

EPS module 270 may be a general communication hub that is configured to distribute events released by various other components of FIG. 2. In some embodiments, all or at least some of the other modules depicted in FIG. 2 may generate events that indicate some form of result/determination/computation/decision from that module. These events may be sent, or "published," to EPS module 270. All or some of the other modules depicted in FIG. 2 may elect to receive, or "subscribe to," any event from any other module. When EPS module 270 receives an event, it may send data indicative of the event (e.g., forward the event) to all modules that have subscribed to that event.

In some embodiments, EPS module 270 may be in communication with one or more databases, such as database 272 and/or archive 274 (which may be optional). In some embodiments, EPS module 270 may accept remote procedure calls ("RPC") from any module to provide access to information stored in one or more databases 272 and/or 274, and/or to add information (e.g., alerts) received from other modules to databases 272 and/or 274. Database 272 (which may be the same as subject reference database 412 in some embodiments) may store information contained in alerts, publications, or other communications sent/broadcast/transmitted by one or more other modules in FIG. 2. In some embodiments, database 272 may store, for instance, subject reference templates associated with patients and/or their initial vital signs, updated vital signs (acquired by vital sign acquisition camera 276), and/or patient acuity measures. Optional archive 274 may in some embodiments store the same or similar information for a longer period of time.

It will be apparent that various hardware arrangements may be utilized to implement the patient monitoring system 252. For example, in some embodiments, a single device may implement the entire system 252 (e.g., a single server to operate the camera 276 to perform the vital signs acquisition functions 260-266 and to perform the vital sign(s) analysis and alerting functions including deterioration detection 268 and patient queue management 258). In other embodiments, multiple independent devices may form the system 252. For example, a first device may drive the vital sign acquisition camera 276 and implement functions 260-266 while another device(s) may perform the remaining functions. In some such embodiments, one device may be local to the waiting room while another may be remote (e.g., implemented as a virtual machine in a geographically distant cloud computing architecture). In some embodiments, a device (e.g., including a processor and memory) may be disposed within the vital sign acquisition camera 276 itself and, as such, the camera 276 may not simply be a dumb peripheral and, instead may perform the vital signs functions 260-266. In some such embodiments, another server may provide indications (e.g. identifiers, full records, or registered facial images) to the camera 276 to request that vitals be returned for further processing. In some such embodiments, additional functionality may be provided on-board the camera 276 such as, for example, the deterioration detection 268 (or preprocessing therefor) and/or patient queue module 258 management may be performed on-board the camera 276. In some embodiments, the camera 276 may even implement the HIS interface 250 or EPS 270. Various additional arrangements will be apparent.

Figure 3:
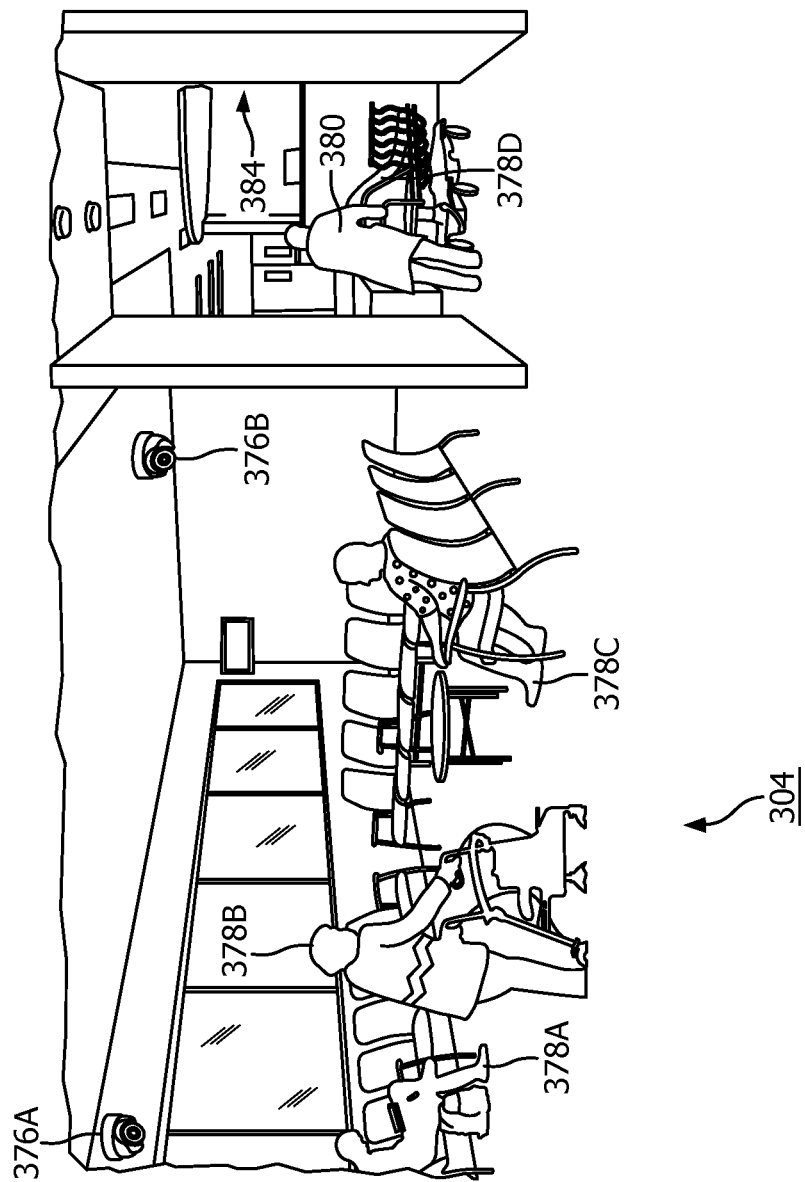
FIG. 3 depicts an example scenario in which disclosed techniques may be practiced, in accordance with various embodiments.

FIG. 3 illustrates an example scenario in which disclosed techniques may be implemented to identify patients 378A-C in a waiting room 304 for monitoring purposes. In this example, three patients 378A-C are waiting in a hospital waiting room 304 to be attended to by medical personnel 380. Two video cameras 376A, 376B are mounted on a surface (e.g., ceiling, wall) of waiting room 304. The two video cameras 376A, 376B may be used to monitor patients 378 in waiting room 304. The patients 378A-C may each be assigned a patient acuity measure by triaging medical personnel (not depicted) based on a preliminary patient condition analysis. As the patients 378 wait for an attending physician, the two video cameras 376A, 376B may capture digital image(s) that are analyzed using techniques described herein to identify patients selected for monitoring. The same video cameras (assuming they are configured to unobtrusively acquire vital signs) or different video cameras may then be operated to monitor patients 378 as described above, e.g., to detect patient deterioration. In some embodiments, a patient acuity measure associated with a patient may be updated by medical personnel in response to detection by patient monitoring system (more specifically, deterioration detection module 268) that a patient has deteriorated. In various embodiments, when a new patient enters waiting room 304, a new round of patient monitoring and prioritization may be performed, e.g., by patient monitoring system 252. The patient queue may be automatically updated, e.g., by patient queue module 258, each time a new patient enters waiting room 304. Additionally or alternatively, medical personnel may manually update the patient queue to include a newly-arrived patient after triaging.

Techniques described herein are not limited to hospital waiting rooms. There are numerous other scenarios in which techniques described herein may be implemented to identify/locate subjects in digital images or videos. For example, disclosed techniques may also be used for security monitoring of crowds in airports, arenas, border crossings, and other public places. In such scenarios, rather than monitoring patients to determine patient acuity measures, subjects may be identified for other purposes, such as risk assessments or post-event investigation. Techniques described herein may also be applicable in scenarios such as in fitness environments (e.g., gyms, nursing homes) or other surveillance scenarios (e.g., airports, border crossings, etc.) in which identification of individual subjects depicted in digital images may be implemented. For example, in airports, subjects waiting at gates could be identified, for example, by comparing images of subjects waiting at gates to subject reference templates obtained at check-in. In addition, techniques described herein may be used to identify patients who left without being seen, without requiring that patients' faces be visible.

Figure 4:
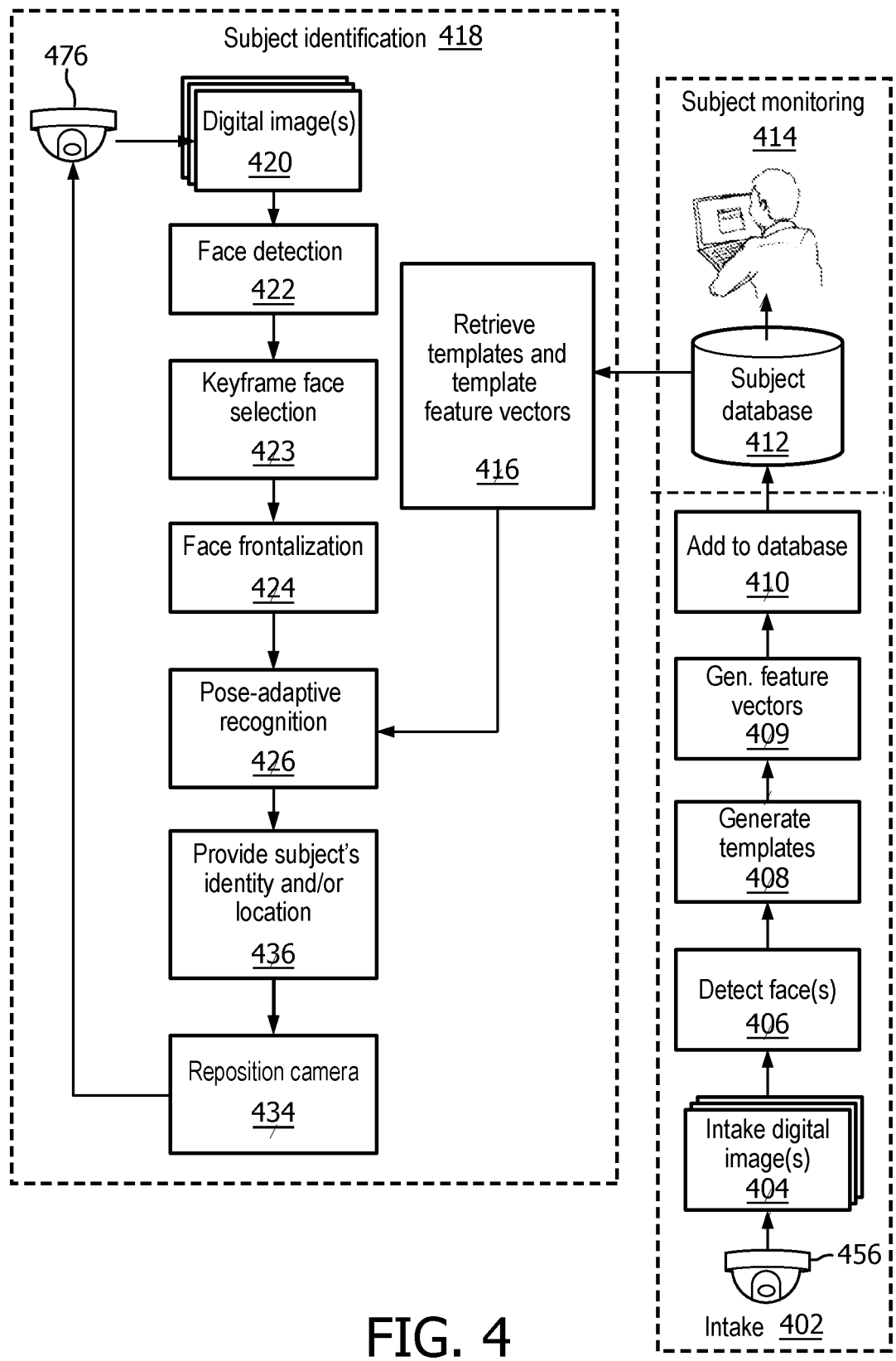
FIG. 4 depicts example components and operations for performing various aspects of the present disclosure.

FIG. 4 schematically depicts, at a relatively high level, an example of components configured with selected aspects of the present disclosure, as well as example interactions between those components. In various embodiments, one or more of these components may be implemented using any combination of hardware and software, e.g., as part of patient monitoring system 252 in FIG. 2 and particularly as part of patient capture module 254 and patient identification module 260. For example, the components of FIG. 4 may be used at block 108 of FIG. 1 to register a subject such as a patient in a subject reference database 412. Along with the subjects' intake information (e.g., age, gender, name, initial vital signs, etc.), any number of "subject reference templates" that comprise digital images of the subject's face from multiple views (e.g., different angles, different facial expressions, different lighting conditions, different head positions, etc.) may be selected and associated with the subject in the subject reference database 412, e.g., by way of a medical record number ("MRN"). These subject reference templates (and as described below, template feature vectors generated from these subject reference templates) may then be used later, e.g., by patient identification module 260, to identify the subject in an area such as a waiting room using another camera (e.g., vital sign acquisition cameras 276, 376) that captures the waiting room in its field of view. Once the subject is identified, the subject's location can be used for various purposes, such as being contacted by medical personnel, having vital signs unobtrusively acquired, etc.

Starting at bottom right, an intake routine 402 is depicted that includes operations for intake of a newly-registered subject (e.g., registering and/or triaging a new patient) and adding that subject to a subject reference database 412, in accordance with various embodiments. A first camera 456 may be configured to capture one or more of what will be referred to herein as "intake" digital images 404 (e.g., individual images and/or a stream of images such as a video stream). First camera 456, which may correspond to camera 256 in FIG. 2 in some instances, may take various forms, such as a webcam positioned in the intake area (e.g., registration and/or triage), a camera integral with a computing device operated by intake personnel (e.g., a triage nurse), etc. This image capture may be un-intrusive to both the intake personnel and the subject, as it may occur automatically with little or no human intervention (although this is not meant to be limiting).

Figure 6:
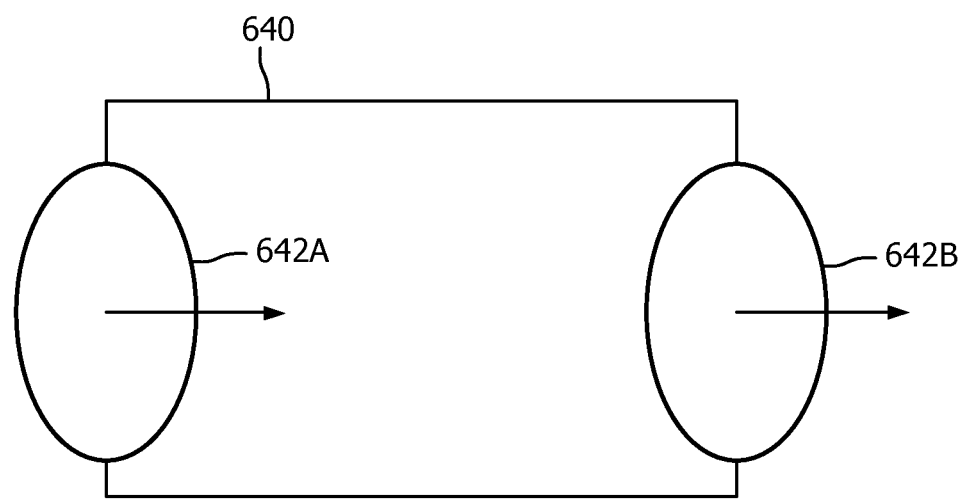
FIG. 6 depicts an example of how a subject may be detected entering and/or leaving a camera's field of view, in accordance with various embodiments.

At block 406, intake digital image(s) 404 may be analyzed, e.g., by one or more computing systems operably coupled with camera 456 (e.g., patient capture module 254 in FIG. 2) to detect one or more portions of digital images 404 that depict a face of a subject currently located in an intake area (e.g., registration and/or triage). FIG. 6 demonstrates one example technique for detecting the subject's face. Other techniques may include, for example, genetic algorithms, eigen-face techniques, etc. In some embodiments, one or more of the intake digital image(s) 404 may be cropped or otherwise altered to focus on the subject's face, although this is not required.

Figure 5:
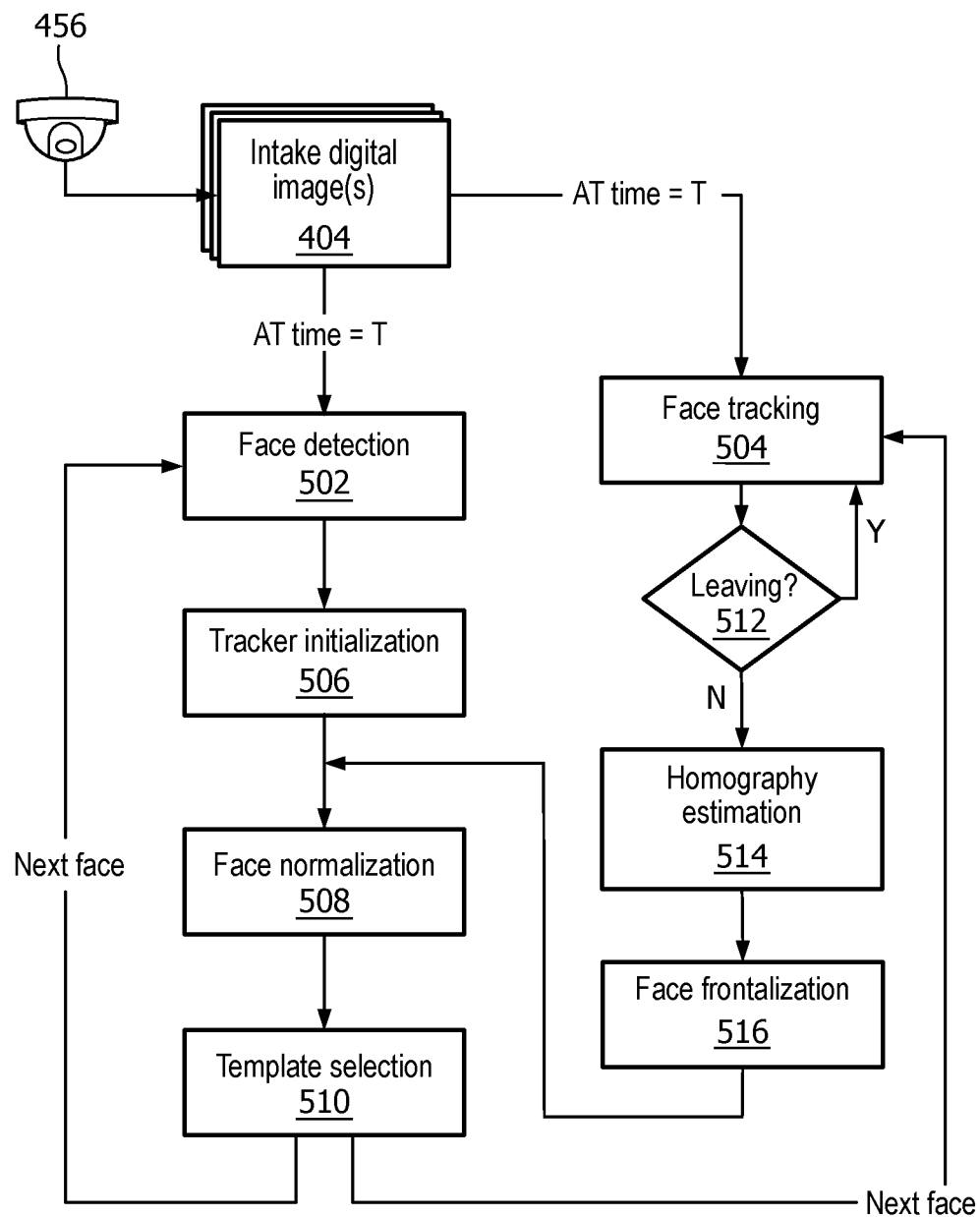
FIG. 5 depicts an example of how subject reference templates may be generated from intake digital images, in accordance with various embodiments.
Figure 8:
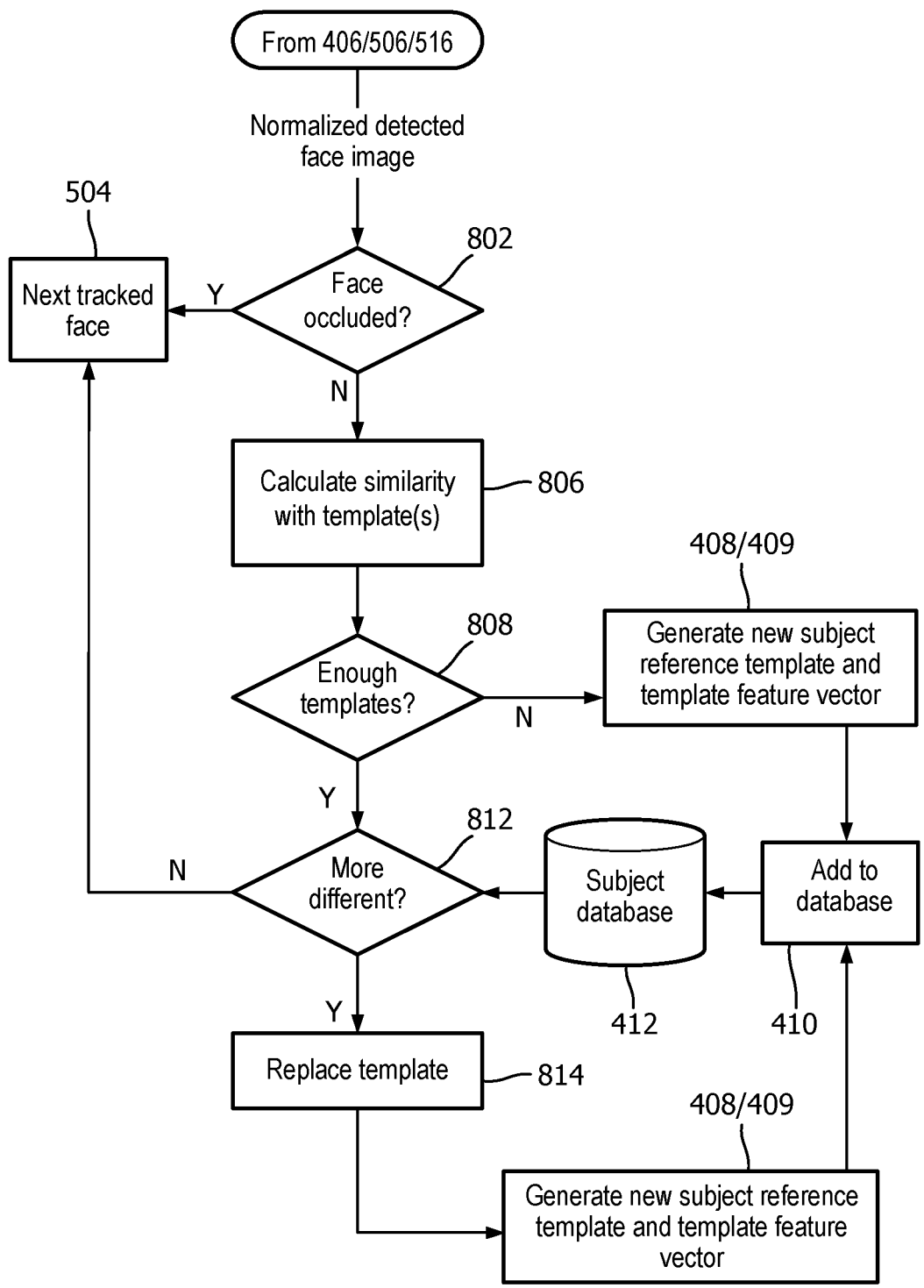
FIG. 8 depicts, in greater detail than FIG. 5, an example of how subject reference templates may be selected from intake digital images, in accordance with various embodiments.

At block 408, a subset of intake digital images that depict multiple different views of a face of the subject may be selected from plurality of intake digital images 404. The selected subset may be used to generate subject reference templates that are used to visually identify/locate the subject later. In some embodiments, the subset of intake digital images used to generate the subject reference templates may be selected based on being sufficiently dissimilar to one or more other intake digital images. FIGS. 5 and 8 below demonstrate example techniques for selecting subsets of intake images for generation of subject reference templates.

In some embodiments, at block 409, the subject reference templates generated at block 408 may be applied as input across a machine learning model, such as a convolutional neural network, to generate what will be referred to herein as "template feature vectors." These template feature vectors may include a variety of features in addition to or instead of the raw data of the subject reference templates. Convolutional neural networks in particular have recently shown improvements over other face recognition approaches. A convolutional neural network may be trained with millions (or more) of face images that include a variety of head poses, facial expressions, lighting conditions, etc., to ensure that the convolutional neural network is usable to generate template feature vectors (and other feature vectors described below) that are more discriminative than the source image alone. In some embodiments, the convolutional neural network may comprise a stack of convolution, regularization, and pooling layers. In some embodiments, one or more graphical processing units ("GPUs") may be employed to perform feature extraction using the convolutional neural networks, as they may be able to do so more efficiently than standard central processing units ("CPUs").

Examples of suitable convolutional neural networks that may be employed to generate various feature vectors described, as well as how they may be trained, are described in O. M. Parkhi, A. Vedaldi, A. Zisserman, *Deep Face Recognition*, British Machine Vision Conference (2015), Yaniv Taigman, Ming Yang, Marc'Aurelio Ranzato, Lior Wolf, *DeepFace: Closing the Gap to Human-Level Performance in Face Verification*, IEEE International Conference on Computer Vision and Pattern Recognition (2014), and Florian Schroff, Dmitry Kalenichenko, James Philbin, *FaceNet: A Unified Embedding for Face Recognition and Clustering*, IEEE International Conference on Computer Vision and Pattern Recognition (2015). In various embodiments, the convolutional neural networks may be trained by minimizing a softmax loss at the last network layer with each subject identity as a unique class label. The loss may then be back-propagated to all previous layers to gradually update all the coefficients in each layer. The back-propagation may be iteratively executed, e.g., thousands of times. During each iteration, as few as dozens or hundreds of face images may be randomly sampled from the collected millions of training face images to be used for the loss minimization.

At block 410, the generated subject reference templates and corresponding template feature vectors may be stored, e.g., in subject reference database 412, in association with the subject. In various embodiments, the generated subject reference templates and template feature vectors may be stored in subject reference database 412 in association with information related to the subject, e.g., by way of the aforementioned MRN. More generally, subject reference database 412 may store subject reference templates (and associated template feature vectors) related to a plurality of subjects, such as a plurality of registered patients in waiting room 104 that may be awaiting medical treatment. In other embodiments, template feature vectors associated with registered subjects may be generated on an as-needed basis.

A subject identification routine 418 is depicted at top left that may be performed, for instance, by patient identification module 260 of FIG. 2 using another camera 476, which may or may not take the form of a vital sign acquisition camera described previously. Patient identification routine 418 may be performed at various times in response to various events, periodically, continuously, etc. In some embodiments, a subject may be sought out as part of a subject monitoring routine 414, in which personnel such as a nurse issues a query seeking to locate a particular subject. In other embodiments, subject identification routine 418 may be performed continuously as part of the ongoing effort described previously to monitor patients' acuity. In some embodiments, camera 476 may be cycled through each detected subject to determine the detected subject's identity and associated it with the detected subject's location.

Subject identification routine 418 may begin with the acquisition of digital images 420 (e.g., a video stream) that depict an area in which a queried subject or subjects generally are believed to be, such as waiting room 104. At block 422, one or more portions of the digital image(s) 420 that depict a face of a particular subject in the area may be detected, e.g., by patient identification module 260, as what will be referred to herein as "detected face images." In various embodiments, the operations of block 422 may be performed continuously and/or may be triggered by receipt of the subject query from patient monitoring routine 414. Similar techniques for face detection may be applied at block 422 as were applied at block 406, and will be described in more detail below.

Figure 7:
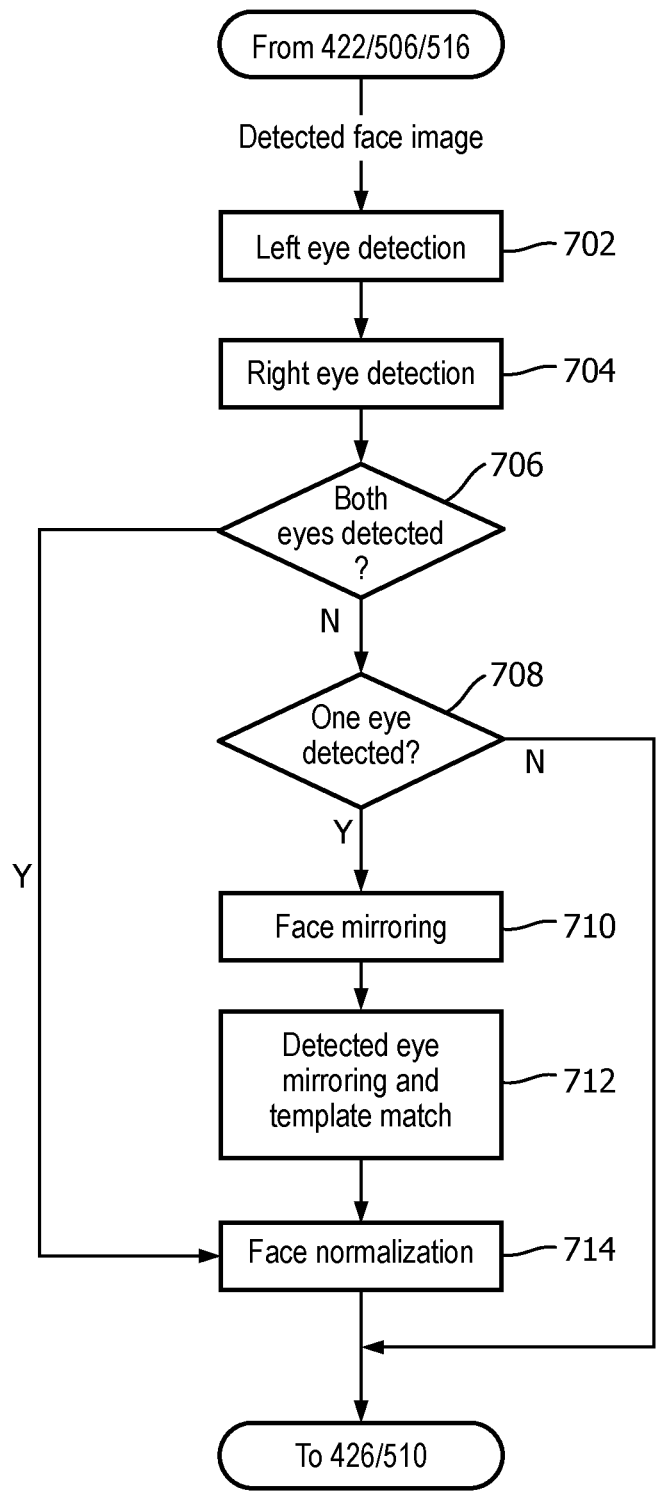
FIG. 7 depicts one example of how a detected face image may be normalized, e.g., to be front-facing, in accordance with various embodiments.

In some embodiments, at block 423, a subset (or "keyframes") of the one or more detected face images generated at block 422 may be selected that represent the greatest variation of depictions of the detected subject's face, e.g., depicting different poses, positions, lighting, facial expressions, etc. In some embodiments, a process similar to that depicted in FIG. 8 may be used to select the subset of detected face images (or "keyframes"). At block 424, one or more operations may be performed to normalize the faces depicted in the detected face images. For example, in some embodiments, geometric warping and/or other similar techniques may be employed to normalize detected faces to be at or near frontal views. FIG. 7 below demonstrates one example technique for normalizing detected faces. Thus, the output of block 424 may be a series of normalized detected face images of a particular subject in the area being monitored.

At block 426, a process referred to herein as "pose-adaptive recognition" may be employed to determine the particular subject's identity by matching the particular subject to a registered subject in subject reference database 412. The process of pose-adaptive face image matching generally relates to incrementally (e.g., as a loop) matching one or more detected face images (which may or may not be pose-normalized) with subject reference templates associated each of a plurality of registered subjects. In some embodiments, a two-stage approach may be employed in each loop increment to determine one or more similarity measures between the detected subject and a currently-considered registered subject.

In the first stage, features of each subject reference template corresponding to a registered subject currently under consideration may be compared to features of each of the detected face images (depicting the detected subject's face) to identify the most similar image pair. Thus, even if a currently-considered registered subject does not really match the detected subject, a closest image pair will nonetheless be identified. In some cases, the closest image pair will be the two images having poses (e.g., position, expression, etc.) that are most similar, even if the subjects look different otherwise.

Then, in a second stage, the most similar image pair (i.e., the detected face image and the subject reference template, associated with the currently-considered registered subject, with the most similar features) may be compared using various image comparison techniques, such as template matching, histogram generation and comparison, perceptual hashes, edge detection plus segmentation, co-occurrence matrices, trained neural networks, etc., to determine one or more similarity measures. These one or more similarity measures between the detected subject and the registered subject currently under consideration may then be compared to similarity measures determined between the detected subject and other registered subjects (during other iterations of the loop). The registered subject with the highest similarity measure(s) may be identified as the detected subject. At block 428, the identity of the detected subject and/or the detected subject's location (e.g., a particular location such as a seat in a waiting room at which the subject is located) may be provided as output. One example process for pose-adaptive recognition will be described in detail in association with FIG. 9.

FIG. 5 depicts one example of how various aspects of the workflow of intake routine 402 of FIG. 4 may be implemented, in accordance with various embodiments. As described above, camera 456 may acquire intake digital images 404, e.g., as a video stream. In some embodiments, intake digital images 404 may depict an intake (e.g., triage) area, although this is not required. The operations depicted in FIG. 5 may be performed at various computing devices, such as a computing device that is operably coupled with camera 456 in or near the intake area.

In the intake (e.g., triage) area where a new subject is assessed (e.g., clinically assessed), for each new intake digital image (e.g., frame of a video stream) captured by camera 456, at blocks 502 and 504, respectively, face detection (e.g., of a new face) and face tracking (e.g., of a face detected in a previous intake digital image) may be performed in parallel. This ensures that a face of each subject in the intake area is detected, no matter which subject entered first. For each newly detected face, at block 506, a new face tracker is launched. This new face tracker will start its analysis at the next image frame. Then, at block 508, the newly detected face is normalized, e.g., to a near-frontal view (normalization is demonstrated in more detail in FIG. 7).

In some embodiments, this normalized detected face may be deemed a subject template candidate. Then, the new subject reference template candidate may be compared, e.g., at block 510, with existing subject reference template candidates (e.g., acquired from previous image frames), if any yet exist. Various criteria may be used to determine whether to keep the new subject reference template candidate, e.g., as a replacement of another previously-captured subject reference template candidate, or to discard the new subject reference template candidate. Ultimately, only the most representative subject reference templates candidates may be selected and retained in subject reference database 412. FIG. 8 demonstrates, in greater detail, one example of how intake digital images may be selected (510) for use in generating subject reference templates.

Turning now to face tracking block 504, for each tracked face previously detected in each intake image frame, at block 512, it may be determined whether the corresponding subject is leaving the camera's field of view. FIG. 6 depicts one example of how a determination may be made of whether a subject is leaving. If the answer at block 512 is yes, then operation passes back to block 504 and the next tracked face is selected. If the answer at block 512 is no, then at block 514, homography estimation may be performed, e.g., to estimate a three-dimensional head pose of the tracked face in the current intake image frame. Based on the estimated pose, the tracked face image in the current frame may be "frontalized" (removing the pose effect on face appearance) at block 516. Control may then pass to block 508.

FIG. 6 demonstrates one example technique for detecting a subject's face, e.g., during intake (e.g., at block 406) or later during subject monitoring (e.g., at block 422). A camera's field of view ("FOV") 640 is shown, and may be associated with any camera described herein, such as camera 456 or camera 476. FIG. 6 illustrates the both detection of a subject (642A) entering and a subject (642B) leaving. Both situations only happen when the subject's face is partially visible in FOV 640. The presence of a subject may be detected, for instance, by measuring the overlapping ratio of a face region to FOV 640. If the ratio is less than a particular number, such as one, and is increasing compared to the previous frame(s), the subject may be determined to be entering. Otherwise, if the ratio is greater than one and is decreasing compared to the previous frame(s), the subject may be determined to be leaving. If either of the two situations lasts for a predetermined time interval, such as five seconds, it is possible to determine that the subject has entered or left.

FIG. 7 depicts details of one example face normalization routine, e.g., that may be performed at block 424 of FIG. 4 and/or block 508 of FIG. 5. Input may take the form of a detected face image, e.g., from block 422 of FIG. 4 and/or from block 506/516 pf FIG. 5. Output may be a normalized detected face image. At blocks 702 and 704, left and right eye detection operations may be performed (operations 702 and 704 may also be performed in the reverse order, or in parallel). These operations may include a variety of image processing techniques, such as edge detection, template matching, Eigenspace methods, Hough transforms, morphological operations, trained neural networks, etc. At block 706, if both eyes are successfully detected, control may pass to block 714, at which point the face may be normalized (e.g., geometric warping may be applied to the detected face image to make the face approximately frontal facing). From block 714, control may pass, for instance, to block 426 of FIG. 4 or to block 510 of FIG. 5.

If the answer at block 706 is no, then at block 708 it may be determined whether either eye was detected. If the answer is no, then control may pass downstream of operation 714, in some instances a failure event may be raised, and then control may proceed, e.g., to block 426 of FIG. 4 or to block 510 of FIG. 5. If only one eye was successfully detected at blocks 702-704, then at block 710, the detected eye region may be mirrored horizontally, and the mirror eye patch may be searched, e.g., using template matching, to locate the other eye. Then, operation may proceed to block 714, which was described previously.

FIG. 8 depicts one example of how detected face images may be selected as subject reference templates, e.g., for inclusion in subject reference database 412, at block 408 of FIG. 4 and block 510 of FIG. 5. Control may pass to the operations of FIG. 8 from various locations, such as block 406 of FIG. 4, block 508 of FIG. 5 (if the detected face image under consideration is newly detected in the current intake digital image frame), and/or block 516 of FIG. 5 (if the detected face image under consideration was detected in a prior intake digital image frame and is currently being tracked). At block 802, it may be determined whether the face is occluded. If the answer is yes, then control may pass to block 504, at which point the next tracked face (if any) may be analyzed.

If the answer at block 802 is no, then at block 806, image similarities between the current detected face image and any existing subject reference templates for the current subject may be determined. At block 808, it may be determined whether there are yet enough subject reference templates collected for the current subject. Various numbers of subject reference templates may be selected for each new subject. In some embodiments, as many as nine subject reference templates may be collected. While collecting more subject reference templates is feasible, diminishing returns may be experienced after some point.

If there are not yet enough subject reference templates collected for the current subject, then at blocks 408-410 (same as FIG. 4), the current detected face image may be used to generate a subject reference template (408), a corresponding template feature vector may be generated (409), and both may then be added (410) to subject reference database 412. However, at block 808, if there are already enough templates collected, then in some embodiments, it may be determined whether the current detected face image is sufficiently different from previously-collected subject reference templates of the current subject to warrant replacing a previously-collected subject reference template. For example, at block, at block 812, a determination may be made of whether the current detected face image is more dissimilar from each previously-collected subject reference template than any of the previously-collected subject reference templates are from each other. If the answer is yes for a particular subject reference template, then the current detected face image may be used to generate a new subject reference template (409) that replaces the particular subject reference template in subject reference database 412. For example, a corresponding template feature vector may be generated 409, and the template and feature vector may be added (410) to subject reference database 412.

The operations of FIG. 8 (and more generally, the operations of FIG. 5) are repeated for every intake digital image captured by camera 456, and each subject may be tracked, for instance, until they leave the intake area (block 512). Consequently, of the total number of intake digital images acquired while the subject is in FOV 640 of camera 456, then intake digital images having the most suitably (e.g., most diverse) views may be selected to generate subject reference templates for that particular subject. As mentioned previously, these subject reference templates may be used later, e.g., in response to a subject being queried at subject monitoring routine 414.

Figure 9:
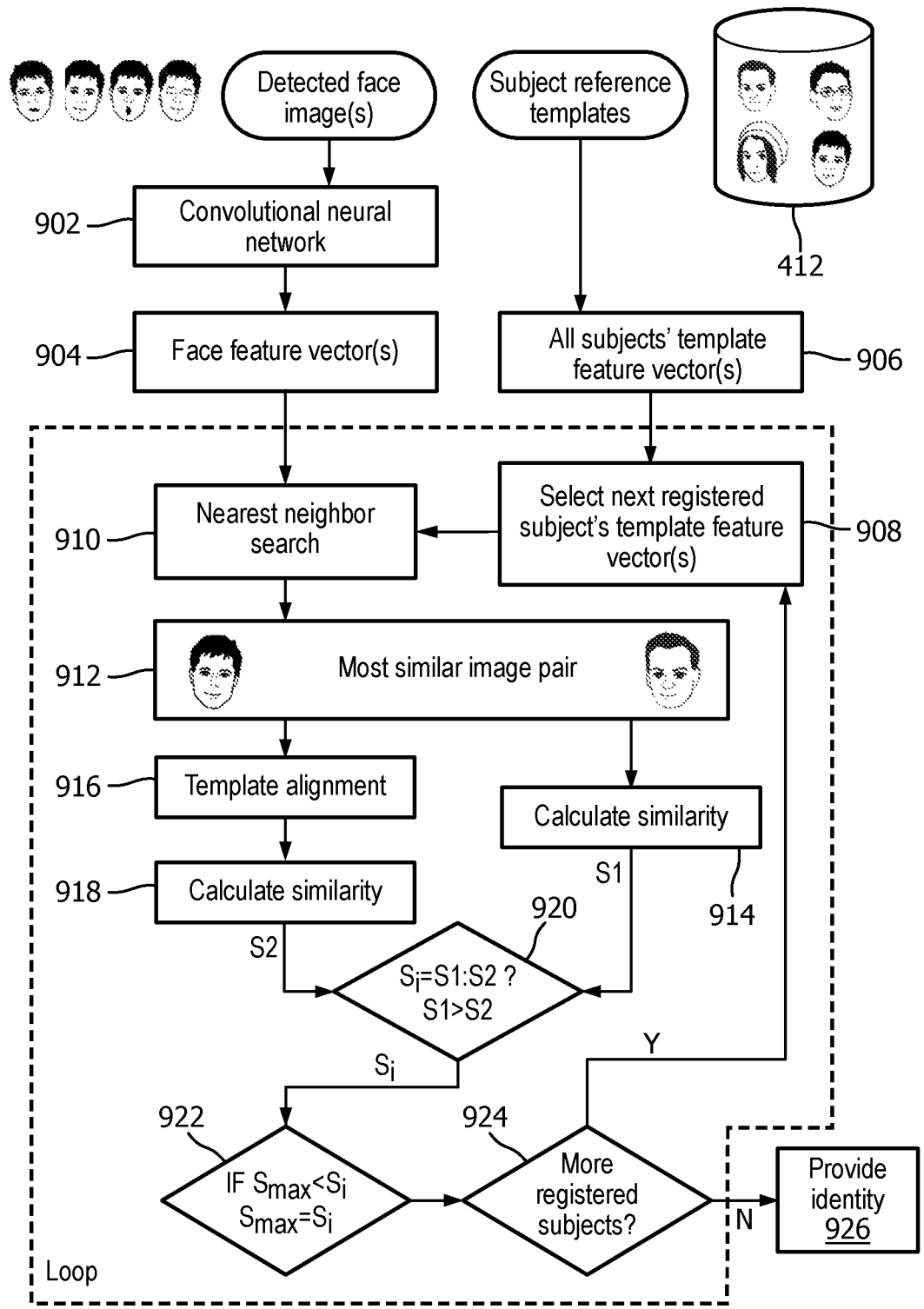
FIG. 9 depicts one example of how subjects may be identified in an area being monitored, in accordance with various embodiments.

FIGS. 5 and 8 relate to collecting subject reference templates and corresponding template feature vectors for each subject to be stored in subject reference database 412. FIGS. 6 and 7 relate to both to collecting subject reference templates and using those subject reference templates to identify subjects in areas downstream from intake areas, such as hospital waiting rooms. FIG. 9 relates to the latter. In particular, FIG. 9 depicts one example of operations that may be performed as part of identifying subjects such as patients in an area (e.g., waiting room 104) being monitored.

In FIG. 9, two inputs are received: the current detected face image(s) under consideration and subject reference templates from subject reference database 412. At block 902, the detected face image(s) may be applied as input across a machine learning model, such as the convolutional neural network described above, to generate (at block 904) so-called "face feature vectors" associated with each detected face image. In some embodiments, the same convolutional neural network(s) may be used as was used at block 409 of FIG. 4 to generate the template feature vectors that are stored in subject reference database 412 with the subject reference templates. Meanwhile, at block 906, all registered subjects' template feature vectors may be retrieved and/or located in subject reference database 412. In other embodiments, all registered subjects' template feature vectors may be generated on the fly, e.g., contemporaneously with operations of block 902 using the same convolutional neural network.

In some embodiments, blocks 908-924 may be performed in a loop, wherein during each iteration of the loop, a different registered subject (referred to herein as the "currently-considered registered subject") is considered. At block 908, the next registered subject may be set as the currently-considered registered subject, and template feature vectors associated with the currently-considered registered subject may be selected, e.g., from all registered subjects' template feature vectors. At block 910, each of the face feature vectors (block 904) may be compared with each of the template feature vectors selected at block 908 for the currently-considered registered subject to identify the closest match. In some embodiments, these comparisons may be performed as a nearest neighbor search. In some embodiments, the face feature vector and the template feature vector that have the lowest (e.g., Euclidian) distance (e.g., determined using dot product, cosine similarity, etc.) between them may represent the closest match. A respective detected face image and subject reference template that correspond to (i.e., were used to generate) the closest matching feature vectors may then be identified at block 912, and will be referred to herein as the "most similar image pair" for the currently-considered registered subject. This ends the aforementioned first stage of the analysis of FIG. 9 for the currently-considered registered subject.

The second stage of analysis for the currently-considered registered subject begins at blocks 914 and 916. At block 914, a similarity measure S1 is calculated between the most similar image pair. Any of the aforementioned techniques for determined similarity measures between images may be employed. At block 916, which may be performed in parallel with the operations of block 914 in some embodiments, a version of the detected face image of the most similar image pair may be generated that is geometrically aligned (e.g., warped) with the subject reference template of the most similar image pair, e.g., to alleviate any geometric difference. At block 918, another similarity measure S2 may be calculated between the version of the given detected face image that is geometrically aligned with the subject reference template and the subject reference template of the most similar image pair.

At block 920, the greater of S1 and S1 may selected as a temporary value $S_i$ (wherein i represents a positive integer that corresponds to the ith registered subject, which is the currently-considered registered subject). At block 922, a maximum similarity measure $S_{max}$ found amongst all the registered subject so far is compared to $S_i$ (if the currently-considered registered subject is the first to be considered, then $S_{max}$ may be set to zero initially). If $S_i$ is greater than $S_{max}$, then $S_{max}$ may be set to $S_i$ and the currently-considered registered subject may be considered the closest match for the detected subject so far (and an identifier associated with that registered subject may be saved); otherwise $S_{max}$ retains its previous value. As each of the registered subjects is considered, $S_{max}$ may continue to increase if any new most similar image pairs are more similar than previous most similar image pairs. At block 924, if there are more registered subjects, then control may pass back to block 908 and the next iteration of the loop may proceed for the next registered subject (i+1). If at block 924 there are no more registered subjects, then the loop may be exited, and $S_{max}$ represents the highest similarity of all registered subject to the detected subject. An identifier (e.g., MRN) of the registered subject associated with $S_{max}$ may be provided as the identity of the detected subject at block 926.

Figure 10:
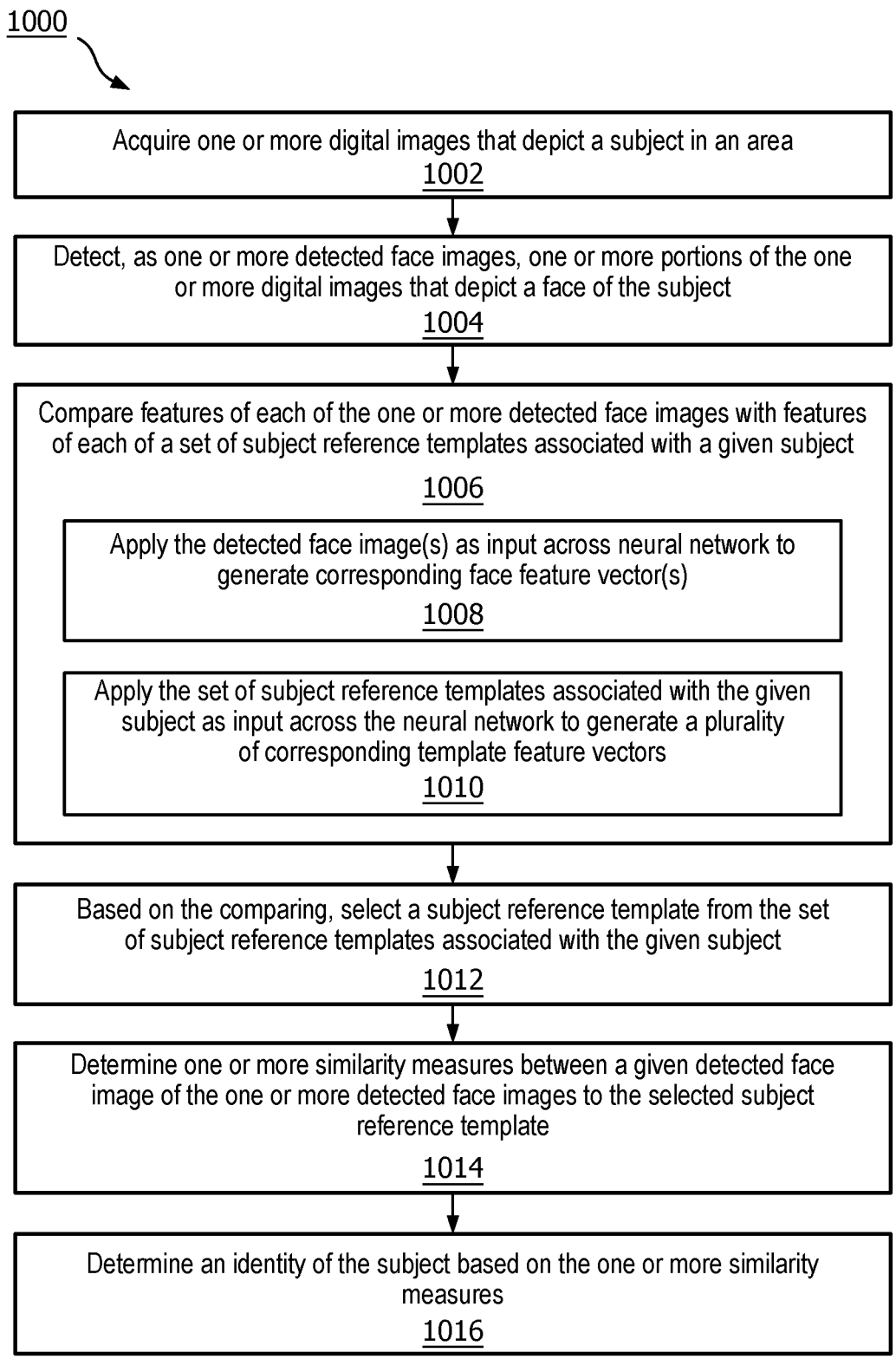
FIG. 10 depicts an example method for performing selected aspects of the present disclosure, in accordance with various embodiments.

FIG. 10 depicts an example method 1000 for practicing selected aspects of the present disclosure, in accordance with various embodiments. For convenience, the operations of the flow chart are described with reference to a system that performs the operations. This system may include various components of various computer systems, including patient monitoring system 252. Moreover, while operations of method 1000 are shown in a particular order, this is not meant to be limiting. One or more operations may be reordered, omitted or added.

At block 1002, the system may acquire, e.g., from one or more cameras (e.g., 276, 376, 476), one or more digital images (e.g., video frames) that depict a subject in an area such as waiting room 104. For example, in some embodiments, the system may acquire a video feed that includes a plurality of digital images acquired by a digital camera. At block 1004, the system may detect, as one or more detected face images, one or more portions of the one or more digital images that depict a face of the subject. In various embodiments, techniques similar to those that were employed at block 406 of FIG. 4 (of which one example is described in more detail in FIG. 6) may be used to detect faces. In some embodiments, head poses that are as much as forty to forty five degrees from facing the camera may be usable to detect faces. As noted above, in some embodiments, "keyframes" of multiple digital images (e.g., a video stream) may be selected that depict a variety of different poses, facial expressions, etc. of the detected subject. And in various embodiments, the digital images (e.g., the keyframes) may be analyzed using various facial detection techniques (e.g., template comparisons) and may be cropped, have their backgrounds removed, etc., so that the detected face images only include the subject's face.

At block 1006 (which begins stage one of the pose-adaptive recognition analysis), the system may compare features of each of the one or more detected face images with features of each of a set of subject reference templates associated with a given subject. In some embodiments, the operations of block 1006 may include, at block 1008, applying the one or more detected face images as input across a neural network (e.g., a convolutional neural network) to generate one or more corresponding face feature vectors. Additionally or alternatively, in some embodiments, the operations of block 1006 may include, at block 1010, applying the set of subject reference templates associated with the given subject as input across the neural network to generate a plurality of corresponding template feature vectors. In other embodiments, the operations of block 1010 may have been performed previously, e.g., during registration/triage or immediately after (e.g., at block 409) and so the plurality of corresponding template feature vectors may simply be retrieved from subject reference database 412.

Based on the comparing, at block 1012, the system may select a subject reference template from the set of subject reference templates associated with the given subject. For example, as described above with respect to FIG. 9, the system may select the subject reference template and detected face image that (i.e., the "most similar image pair") correspond to the face feature vector and template feature vector with the smallest distance (e.g., Euclidian) between them.

At block 1014 (which begins stage two or the pose-adaptive recognition analysis), the system may determine one or more similarity measures (e.g., S1, S2 of FIG. 9) between a given detected face image (e.g., the detected face image of the "most similar image pair") of the one or more detected face images to the subject reference template selected at block 1012. In some embodiments, two similarity measures—i.e., S1 and S2 described above—may be computed. Based on these one or more similarity measures (and in many embodiments further based on similarity measures associated with other registered patients), at block 1016, the system may determine an identity of the subject. For example, the one or more similarity measures may be calculated for each registered subject, and the identity of the registered subject with the greatest one or more similarity measures may be attributed to the subject.

The subject's identity determined at block 1016 may be used for various purposes. In some embodiments, the location of the subject depicted in the original digital images (acquired at block 1002) may be determined, e.g., based on PTZ settings of the camera that captured the digital images. For example, in some embodiments, the camera may be configured to scan through a plurality of locations, such as chairs in waiting room 104, looking for subjects at each location. When a subject is detected at a particular location and then matched to a registered subject, the subject's identity may be provided, e.g., as audio or visual output to a duty nurse or other medical personnel, along with a location of the subject. In some embodiments, the identity/location may be output to other modules of patient monitoring system 252.

In other scenarios, a location of a particular registered subject (e.g., a queried subject) may be desired, e.g., so that the subject's vital signs can be monitored (e.g., unobtrusively using camera 276), the subject can be taken to see a doctor, etc. In such a situation, method 1000 may be performed for each subject that is detected by one or more cameras monitoring an area such as waiting room 1004 until the sought-after subject is located. In some such scenarios, if the queried subject is not found—e.g., because the subject was admitted into a treatment area of an emergency department or the subject left without being seen—pertinent personnel (e.g., hospital staff) may be notified. If the subject left temporarily, e.g., to use the restroom, the subject may be reinserted into the patient queue described above so that they can be monitored at a later time.

Figure 11:
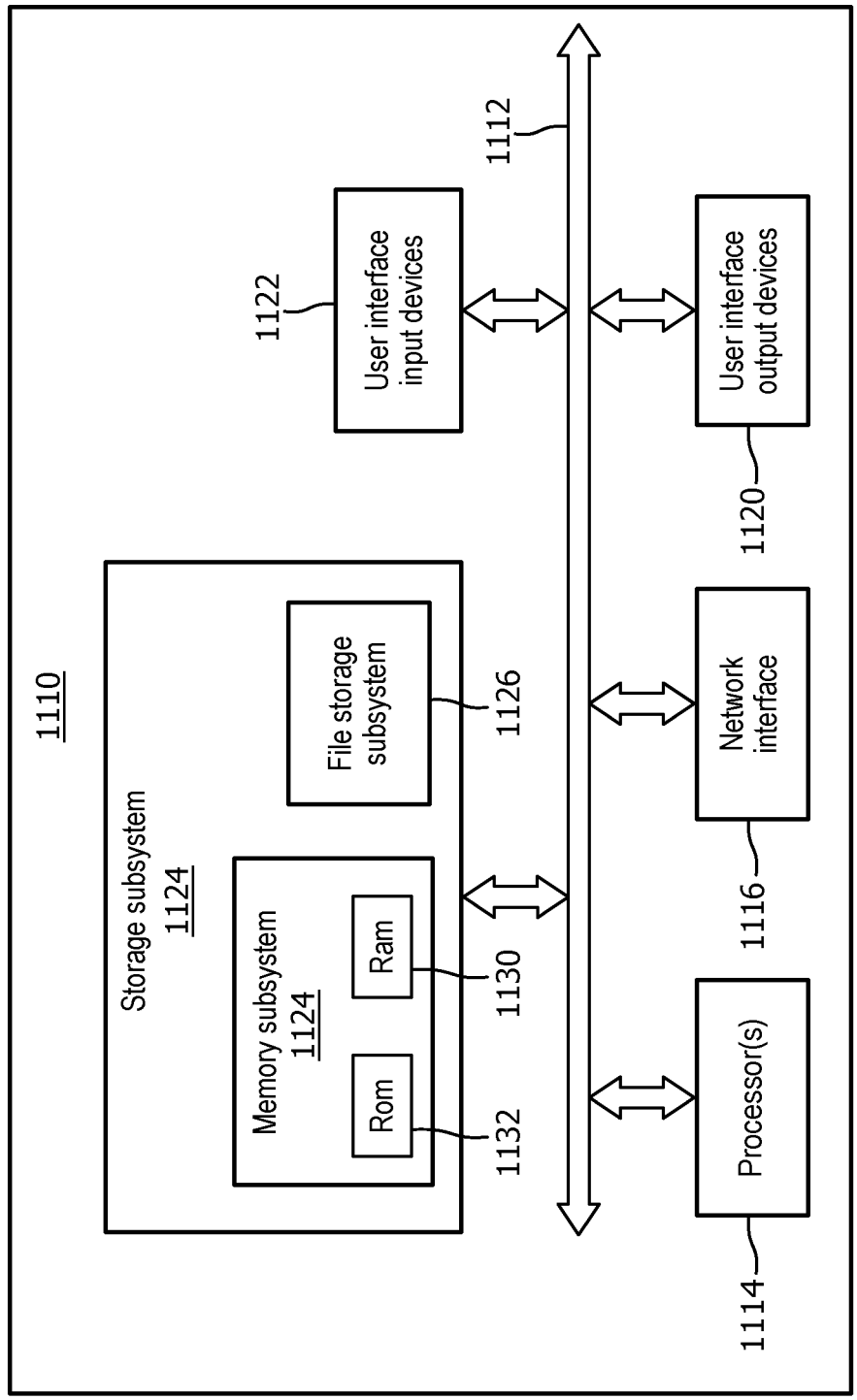
FIG. 11 depicts components of an example computer system.

FIG. 11 is a block diagram of an example computer system 1110. Computer system 1110 typically includes at least one processor 1114 which communicates with a number of peripheral devices via bus subsystem 1112. As used herein, the term "processor" will be understood to encompass various devices capable of performing the various functionalities attributed to components described herein such as, for example, microprocessors, GPUs, FPGAs, ASICs, other similar devices, and combinations thereof. These peripheral devices may include a data retention subsystem 1124, including, for example, a memory subsystem 1125 and a file storage subsystem 1126, user interface output devices 1120, user interface input devices 1122, and a network interface subsystem 1116. The input and output devices allow user interaction with computer system 1110. Network interface subsystem 1116 provides an interface to outside networks and is coupled to corresponding interface devices in other computer systems.

User interface input devices 1122 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 1110 or onto a communication network.

User interface output devices 1120 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 1110 to the user or to another machine or computer system.

Data retention system 1124 stores programming and data constructs that provide the functionality of some or all of the modules described herein. For example, the data retention system 1124 may include the logic to perform selected aspects of FIGS. 4-10, and/or to implement one or more components of patient monitoring system 252, including patient identification module 260, patient capture module 254, etc.

These software modules are generally executed by processor 1114 alone or in combination with other processors. Memory 1125 used in the storage subsystem can include a number of memories including a main random access memory (RAM) 1130 for storage of instructions and data during program execution, a read only memory (ROM) 1132 in which fixed instructions are stored, and other types of memories such as instruction/data caches (which may additionally or alternatively be integral with at least one processor 1114). A file storage subsystem 1126 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 1126 in the data retention system 1124, or in other machines accessible by the processor(s) 1114. As used herein, the term "non-transitory computer-readable medium" will be understood to encompass both volatile memory (e.g. DRAM and SRAM) and non-volatile memory (e.g. flash memory, magnetic storage, and optical storage) but to exclude transitory signals.

Bus subsystem 1112 provides a mechanism for letting the various components and subsystems of computer system 1110 communicate with each other as intended. Although bus subsystem 1112 is shown schematically as a single bus, alternative implementations of the bus subsystem may use multiple busses. In some embodiments, particularly where computer system 1110 comprises multiple individual computing devices connected via one or more networks, one or more busses could be added and/or replaced with wired or wireless networking connections.

Computer system 1110 can be of varying types including a workstation, server, computing cluster, blade server, server farm, or any other data processing system or computing device. In some embodiments, computer system 1110 may be implemented within a cloud computing environment. Due to the ever-changing nature of computers and networks, the description of computer system 1110 depicted in FIG. 11 is intended only as a specific example for purposes of illustrating some implementations. Many other configurations of computer system 1110 are possible having more or fewer components than the computer system depicted in FIG. 11.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. A method implemented by one or more processors, the method comprising:
    acquiring one or more digital images that depict a subject in an area, wherein the area comprises a waiting room, and the one or more digital images that depict the waiting room are acquired using a camera that is configured to capture the waiting room;

detecting, as one or more detected face images, one or more portions of the one or more digital images that depict a face of the subject;

comparing features of each of the one or more detected face images with features of each of a set of subject reference templates associated with a given subject in a subject reference database, wherein the subject reference database stores subject reference templates related to a plurality of subjects;

based on the comparing, selecting a subject reference template from the set of subject reference templates associated with the given subject;

determining one or more similarity measures between a given detected face image of the one or more detected face images and the selected subject reference template;

determining an identity of the subject based on the one or more similarity measures, and acquiring one or more vital signs and/or physiological parameters of the subject from a vital signs acquisition camera.

2. The method of claim 1, wherein the comparing comprises:

applying the one or more detected face images as input across a neural network to generate one or more corresponding face feature vectors; and applying the set of subject reference templates associated with the given subject as input across the neural network to generate a plurality of corresponding template feature vectors.

3. The method of claim 2, wherein the neural network comprises a convolutional neural network.

4. The method of claim 2, wherein the comparing comprises calculating a plurality of distances between the one or more face feature vectors and the plurality of template feature vectors, wherein the calculating comprises calculating, for each template feature vector of the plurality of template feature vectors, a distance from each of the one or more face feature vectors.

5. The method of claim 4, wherein the selecting is based on a lowest distance of the plurality of distances.

6. The method of claim 5, further comprising selecting the given detected face image from the one or more detected face images based on the lowest distance.

7. The method of claim 1, wherein the comparing comprises comparing features of each of the one or more detected face images with features of each of multiple sets of subject reference templates associated with the plurality of subjects.

8. The method of claim 1, wherein the one or more similarity measures include:

a first similarity measure that is calculated based on a version of the given detected face image that is geometrically aligned with the selected subject reference template; and a second similarity measure that is calculated based directly on the given detected face image;

wherein the identity of the subject is determined based on the greater of the first and second similarity measures.

9. The method of claim 1, wherein the vital signs and/or physiological parameters comprise at least one of temperature, pulse rate, oxygen saturation, respiration rate, posture, or perspiration.

10. A system comprising one or more processors and memory operably coupled with the one or more processors, wherein the memory stores instructions that, in response to execution of the instructions by one or more processors, cause the one or more processors to perform the following operations:

acquiring one or more digital images that depict a subject in an area, where the area comprises a waiting room, and the one or more digital images that depict the waiting room are acquired using a camera that is configured to capture the waiting room;

detecting, as one or more detected face images, one or more portions of the one or more digital images that depict a face of the subject;

comparing features of each of the one or more detected face images with features of each of a set of subject reference templates associated with a given subject in a subject reference database, wherein the subject reference database stores subject reference templates related to a plurality of subjects;

based on the comparing, selecting a subject reference template from the set of subject reference templates associated with the given subject;

determining one or more similarity measures between a given detected face image of the one or more detected face images and the selected subject reference template;

determining an identity of the subject based on the one or more similarity measures, and acquiring one or more vital signs and/or physiological parameters of the subject from a vital signs acquisition camera.

11. The system of claim 10, wherein the comparing comprises:

applying the one or more detected face images as input across a neural network to generate one or more corresponding face feature vectors; and applying the set of subject reference templates associated with the given subject as input across the neural network to generate a plurality of corresponding template feature vectors.

12. The system of claim 11, wherein the neural network comprises a convolutional neural network.

13. The system of claim 11, wherein the comparing comprises calculating a plurality of distances between the one or more face feature vectors and the plurality of template feature vectors, wherein the calculating comprises calculating, for each template feature vector of the plurality of template feature vectors, a distance from each of the one or more face feature vectors.

14. The system of claim 13, wherein the selecting is based on a lowest distance of the plurality of distances.

15. The system of claim 14, further comprising selecting the given detected face image from the one or more detected face images based on the lowest distance.

16. The system of claim 10, wherein the comparing comprises comparing features of each of the one or more detected face images with features of each of multiple sets of subject reference templates associated with the plurality of subjects.

17. The system of claim 10, wherein the one or more similarity measures include:

a first similarity measure that is calculated based on a version of the given detected face image that is geometrically aligned with the selected subject reference template; and a second similarity measure that is calculated based directly on the given detected face image;

wherein the identity of the subject is determined based on the greater of the first and second similarity measures.

18. The system of claim 10, wherein the vital signs and/or physiological parameters comprise at least one of temperature, pulse rate, oxygen saturation, respiration rate, posture, or perspiration.

19. At least one non-transitory computer-readable medium comprising instructions that, in response to execution of the instructions by one or more processors, cause the one or more processors to perform the following operations:

acquiring one or more digital images that depict a subject in an area, wherein the area comprises a waiting room, and the one or more digital images that depict the waiting room are acquired using a camera that is configured to capture the waiting room;

detecting, as one or more detected face images, one or more portions of the one or more digital images that depict a face of the subject;

comparing features of each of the one or more detected face images with features of each of a set of subject reference templates associated with a given subject in a subject reference database, wherein the subject database stores subject reference templates related to a plurality of subjects;

based on the comparing, selecting a subject reference template from the set of subject reference templates associated with the given subject;

determining one or more similarity measures between a given detected face image of the one or more detected face images and the selected subject reference template;

determining an identity of the subject based on the one or more similarity measures, and acquiring one or more vital signs and/or physiological parameters of the subject from a vital signs acquisition camera.

20. The at least one non-transitory computer-readable medium of claim 19, wherein the comparing comprises:

applying the one or more detected face images as input across a convolutional neural network to generate one or more corresponding face feature vectors; and applying the set of subject reference templates associated with the given subject as input across the convolutional neural network to generate a plurality of corresponding template feature vectors.

* * * * *